US011058563B2

(12) United States Patent
Van Langenhove

(10) Patent No.: US 11,058,563 B2
(45) Date of Patent: Jul. 13, 2021

(54) IMPLANT STENT DEVICE

(71) Applicant: MEDICAL DEVELOPMENT TECHNOLOGIES S.A., Fentange (LU)

(72) Inventor: Glenn Van Langenhove, Merelbeke (BE)

(73) Assignee: MEDICAL DEVELOPMENT TECHNOLOGIES S.A., Fentange (LU)

( * ) Notice: Subject to any disclaimer, the term of this patent is extended or adjusted under 35 U.S.C. 154(b) by 64 days.

(21) Appl. No.: 15/768,290

(22) PCT Filed: Oct. 17, 2016

(86) PCT No.: PCT/EP2016/074866
§ 371 (c)(1),
(2) Date: Apr. 13, 2018

(87) PCT Pub. No.: WO2017/064321
PCT Pub. Date: Apr. 20, 2017

(65) Prior Publication Data
US 2018/0296375 A1    Oct. 18, 2018

(30) Foreign Application Priority Data

Oct. 15, 2015   (EP) ...................................... 15189963
Aug. 12, 2016   (EP) ...................................... 16184126

(51) Int. Cl.
*A61F 2/90*         (2013.01)
*A61F 2/06*         (2013.01)
(Continued)

(52) U.S. Cl.
CPC ................ *A61F 2/90* (2013.01); *A61B 18/04* (2013.01); *A61F 2/06* (2013.01); *A61N 1/403* (2013.01);
(Continued)

(58) Field of Classification Search
CPC .......... A61F 2002/825; A61F 2002/826; A61F 2002/828; A61F 2/89; A61F 2250/001;
(Continued)

(56) References Cited
U.S. PATENT DOCUMENTS 5,868,783  A  *  2/1999  Tower ....................... A61F 2/90
                                                             606/194
6,432,127  B1 *  8/2002  Kim ........................ A61B 17/11
                                                             606/198
(Continued)

FOREIGN PATENT DOCUMENTS

WO   WO-2012131107 A1 * 10/2012 ............. A61B 18/04
WO   WO-2013149683 A1 * 10/2013

OTHER PUBLICATIONS

International Search Report and Written Opinion dated Feb. 6, 2017 for International Patent Application No. PCT/EP2016/074866, van Langenhove, "Improved Implant Device," filed Oct. 17, 2016 (9 pages).

*Primary Examiner* — Paul B Prebilic
(74) *Attorney, Agent, or Firm* — Clark & Elbing LLP

(57) ABSTRACT

The present invention concerns a self-expanding implant device comprising a proximal portion at a first longitudinal end, a distal portion at a second longitudinal opposite the first longitudinal end, and a connecting portion between the proximal portion and the distal portion, wherein the proximal portion and the distal portion each comprise a radially self-expanding structure, wherein the connecting portion comprises longitudinally oriented bendable struts, preferably at least 4 struts, more preferably 6 struts or more, which connect the self-expanding structure of the proximal portion with the self-expanding structure of the distal portion, wherein in a fully expanded state, the implant device comprises a maximum implant diameter along a direction perpendicular to the longitudinal direction and wherein the (Continued)

struts of the connecting portion comprise a strut length along the longitudinal direction, characterized in that the strut length is such that when the self-expanding structure of the proximal portion is in a compacted state and the self-expanding structure of the distal portion is not constrained radially, the self-expanding structure of the distal portion reaches a semi-expanded state comprising a diameter which is at least 60% of the maximum implant diameter.

27 Claims, 15 Drawing Sheets

(51) Int. Cl.
    *A61F 2/82*     (2013.01)
    *A61B 18/04*     (2006.01)
    *A61N 1/40*     (2006.01)
    *A61B 18/00*     (2006.01)
    *A61M 25/01*     (2006.01)

(52) U.S. Cl.
    CPC ............... *A61B 2018/00375* (2013.01); *A61B 2018/00577* (2013.01); *A61F 2002/825* (2013.01); *A61F 2250/0001* (2013.01); *A61M 25/01* (2013.01)

(58) Field of Classification Search
    CPC ...... A61F 2250/0018; A61F 2250/0029; A61F 2250/0037; A61F 2250/0001; A61F 2202/9505; A61F 2002/9505; A61F 2/06; A61F 2/90; A61B 18/04; A61B 18/0577; A61B 2560/0242–2560/0247; A61B 2560/0266; A61B 2560/0462; A61B 2560/06–2560/066; A61B 2562/0223; A61B 2562/0271
    See application file for complete search history.

(56) References Cited

U.S. PATENT DOCUMENTS

| | | | |
|---|---|---|---|
| 6,451,052 B1* | 9/2002 | Burmeister | A61F 2/844 623/1.16 |
| 6,764,503 B1* | 7/2004 | Ishimaru | A61F 2/07 606/108 |
| 7,632,303 B1* | 12/2009 | Stalker | A61F 2/90 623/1.15 |
| 2007/0100435 A1* | 5/2007 | Case | A61F 2/2418 623/1.24 |
| 2007/0213810 A1* | 9/2007 | Newhauser | A61F 2/91 623/1.16 |
| 2007/0219613 A1* | 9/2007 | Kao | A61B 17/12022 623/1.11 |
| 2008/0215129 A1* | 9/2008 | Venturelli | A61F 2/91 623/1.11 |
| 2009/0248132 A1 | 10/2009 | Bloom et al. | |
| 2010/0324658 A1* | 12/2010 | Bogert | A61F 2/91 623/1.16 |
| 2011/0224777 A1* | 9/2011 | Von Oepen | A61F 2/91 623/1.16 |
| 2012/0101567 A1* | 4/2012 | Jansen | A61F 2/2418 623/1.16 |
| 2014/0031785 A1* | 1/2014 | Schwagten | A61B 18/04 604/500 |
| 2014/0309731 A1 | 10/2014 | Quadri et al. | |
| 2015/0112421 A1 | 4/2015 | Barnes et al. | |
| 2015/0150621 A1* | 6/2015 | Schwagten | A61B 18/10 606/31 |
| 2015/0150671 A1 | 6/2015 | Gilson et al. | |
| 2021/0038380 A1* | 2/2021 | Tabor | A61F 2/013 |

* cited by examiner

Construction Specification:

| | Material | Diameter (mm) |
|---|---|---|
| 1. Inner Conductor | Silver Plated Copper Clad Steel | 0.2 |
| 2. Dielectric | PTFE | 0.52 |
| 3. Outer Conductor | Silver Plated Copper Braid | |
| 4. Jacket | FEP | 1.17 |

IMPLANT STENT DEVICE

TECHNICAL FIELD

The present invention concerns implant devices, such as stent devices, which can be implanted in vessels and organs. More in particular, the implant devices of the present invention are particularly apt in correctly being placed at a chosen location within the vessel or organ, and this preferably to provide treatment to the walls of the vessel or organ.

BACKGROUND

Implant devices such as stents are typically placed in vessels, e.g. arteries or veins, to keep the vessel open.

Implant devices can also be used to provide local treatment, e.g. to treat the surrounding tissue. An example of a system and implant device for local treatment is disclosed in document WO 2012/131107 A1. Herein a system is disclosed comprising an implant device and external energy-providing means. The system is particularly developed for ablation of a vessel's wall from the inside, more specifically the system comprises implant devices which can be placed in one or more vessels, preferably in the pulmonary veins for the ablation of the wall of one or more pulmonary veins (PV) from the inside, preferably transmural ablation and preferably at the level of the antrum. Hereby, one or more implant devices can be implanted in the vessels and can subsequently be heated by external energy-providing means. The main objective of the ablation is to cause pulmonary vein isolation (PVI). PVI can solve the problem of atrial fibrillation (AF) by electrically isolating the one or more PVs from the heart tissue such that signals do not travel along myocardial sleeves along the PVs. The document thereto discloses a self-expanding implant device, adapted to be implanted and deployed within said vessel; whereby said implant comprises an ablation region along at least a portion of its length, said ablation region being adapted for surface contact with said vessel and said ablation region subtending at least a substantially complete circumferential band and being effective to ablate a signal-blocking path within said vessel upon application of energy to the implant.

By developing an implant device which can be used for PVI, e.g. according to a system and methods disclosed in WO 2012/131107 A1, the present inventors have found that it is not so easy to correctly transport the implant to a predetermined location and to correctly position and fixate the implant at that pre-determined location, which for PVI typically is the antrum of a PV.

Hence, there is a need in the art for an implant device which can be easily transported to a target zone, the target zone being a pre-determined position in e.g. a vessel or organ, where the implant device needs to be positioned, e.g. for keeping the vessel open or for treatment of the vessel's or organ's tissue.

There is also a need for an implant device which can be easily correctly positioned at the target zone and which easily and is correctly fixated at said target zone. Hereby, fixation is of extreme importance if the implant device is used for PVI and the target zone is the antrum of a PV, as the consequences of the implant device moving or being shifted can be dramatic.

The implant device of the present invention solves the problems of the prior art.

Atrial fibrillation (AF) is the most common arrhythmia in human adults. Its incidence gets higher year after year, even if the increase in life expectancy is taken into consideration. It accounts for huge increases in morbidity and mortality. This leads to an increased burden on the health care expenditure.

In the last decade, pulmonary vein isolation (PVI) has become the preferred choice in a variety of cases, due to ongoing side effects of medication, improvement of ablation techniques and patient demand.

PVI is traditionally performed by inserting an ablation catheter via a blood vessel, e.g. via the groin, through the right atrium of the heart, through a hole to the left atrium in order to reach the pulmonary vein(s) (PV). An ablation tip of the ablation catheter is brought into contact with the antrum of the PV which is to be treated. A lesion in the inner wall of the PV can be formed by the ablation tip through use of cryonics or through use of a radiofrequent current sent via the catheter to the tip. The ablation tip is repeatedly repositioned in order to ablate a circumferential path. The resulting scar tissue hereby can form a circumferential signal-blocking path which blocks electrical signals coming from the PVs, which are the main triggers of AF.

PVI is however still hampered by a high recurrence rate, prolonged procedural times, and an intraprocedural complication rate of 1 to 8 percent.

A prior art method describing an improved method and related system and devices for creating a circumferential signal-blocking path in a PV is disclosed in WO 2012/131107 A1. This document discloses systems, devices and methods for the ablation of a vessel's wall from the inside, more specifically to implant devices and to the ablation of the wall of one or more pulmonary veins (PV) from the inside, preferably transmural ablation and preferably at the level of the antrum. Hereby, one or more implant devices can be implanted in the vessels and can subsequently be heated by external energy-providing means. Document WO 2013/149683 A1 discloses an implant for treating atrial fibrillation by multiple ablation of the inner walls of a pulmonary vein via heating, comprising an electrical circuit comprising a pickup coil, a heater coil and a temperature-controlled switch which comprises a closed position and an interrupted position, said pick-up coil arranged for inducing an electrical current through at least part of said electrical circuit to which it is connected under the influence of a time varying magnetic flux through said pickup coil, whereby said heating coil is arranged for subtending a substantially complete circumferential ablation region in a pulmonary vein vessel, for obtaining a substantially complete circumferential signal-blocking lesion on the inner wall of said vessel, and whereby said switch is arranged to change from said closed to said open position when a temperature at or near said implant is higher than a pre-defined ablation temperature. Both documents discloses techniques and technologies which improve upon the traditional ablation methods, in particular with respect to lower recurrence rates, lower procedural times and lower complication rates. Moreover, because of the external energy-providing means which activate the implant device, a second or further ablation can be performed if necessary without invasive surgery as the implant device can remain within the PV. Both documents WO 2012/131107 A1 and WO 2013/149683 are hereby incorporated by reference.

Notwithstanding these improvements, there remains a need in the art for improved implant devices, systems and methods for PVI.

SUMMARY OF THE INVENTION

The present invention provides a self-expanding implant device comprising a proximal portion at a first longitudinal end, a distal portion at a second longitudinal opposite the first longitudinal end, and a connecting portion between the proximal portion and the distal portion. The proximal portion and the distal portion each comprise a radially self-expanding structure. The connecting portion comprises longitudinally oriented bendable struts, preferably at least 4, more preferably 6, which connect the self-expanding structure of the proximal portion with the self-expanding structure of the distal portion. In a fully expanded state, the implant device comprises a maximum implant diameter along a direction perpendicular to the longitudinal direction. The struts of the connecting portion comprise a strut length along the longitudinal direction.

By the term "longitudinal" as used herein, is meant that the direction from a proximal end of the implant to a distal end of the implant, or vice versa. As the implant device is preferably essentially tubular when the implant is expanded, the longitudinal direction coincides with the direction of the tubular axis of the expanded implant.

The strut length is such that when the self-expanding structure of the proximal portion is in a compacted state and the self-expanding structure of the distal portion is not constrained radially, the self-expanding structure of the distal portion can reach a semi-expanded state comprising a diameter which is at least 60% of the maximum implant diameter, preferably at least 70%, more preferably at least 80%, even more preferably at least 90%, yet more preferably about 100% of the maximum implant diameter. Note that the self-expanding structure of the distal portion in a semi-expanded state could also comprise a diameter which is more than 100% of the maximum implant diameter due to skewing of the self-expanding structure when being deployed.

The implant device according to the present invention allows easy and correct transport to the target zone, easy and correct positioning at the target zone and easy and correct fixation at the target zone.

To transport the implant device, it is brought into a fully compacted state. This is possible due to the self-expanding structures of the distal and proximal portion, which allow radial compactification, and due to the longitudinally oriented struts whose orientation is longitudinal in the expanded state as well as in the compacted state, the distances between the struts altering when the implant device is being compacted radially or being expanded radially. The implant device can be brought to the target zone by a catheter delivery system.

When the delivery system has brought the implant device to or near the target zone, the implant device can be deployed, starting with the distal portion, then the connecting portion and finally the proximal portion. This can be achieved by a delivery system comprising a sheath, i.e. a tube-like catheter which radially constrains the implant device to its compacted state initially, and which is carefully retracted when the delivery system has positioned the implant device at or near the target zone. Retraction of the sheathing catheter thus gradually releases the radial constraint on the self-expanding implant device, starting from the distal end to the proximal end.

Due to the specific nature of the implant device, in particular to the strut length being such that when the self-expanding structure of the proximal portion is in a compacted state and the self-expanding structure of the distal portion is not constrained radially, the self-expanding structure of the distal portion can reach a semi-expanded state comprising a diameter which is at least 60% of the maximum implant diameter, preferably at least 70%, more preferably at least 80%, even more preferably at least 90%, yet more preferably about 100% of the maximum implant diameter. Hence, even when the self-expanding structure of the proximal portion is still unsheathed and thus in the compacted state, the self-expanding structure of the distal portion thus reaches a diameter which allows contact and even anchoring of the implant device at the target zone. As one can very accurately position the delivery catheter near the target zone, and the implant device is being anchored at the same time as being deployed, also the implant device itself can be positioned correctly. This is particularly useful when the implant device needs to be positioned at a very specific target zone along a vessel or e.g. at a vessel or organ which does not have a constant diameter at the location of the target zone, such as the antrum of a PV, where the diameter of the vessel can change by a factor of 2 or more within a few centimeters.

In an embodiment, the implant device is adapted to be implanted and deployed within a pulmonary vein.

Further embodiments of the implant device according to the present invention are described in the claims and further below.

The present invention also provides an implant device, external energy-providing means and a system comprising such an implant device and external energy-providing means, for PVI. The present invention also relates to a method for PVI.

The implant device is preferably a self-expanding implant device adapted to be implanted and deployed within a vessel such as a PV, said implant comprising an ablation region along at least a portion of its length, the ablation region being adapted for surface contact with the vessel and for subtending at least a substantially complete circumferential band or a spiraling band and said ablation region effective to ablate a signal-blocking path within the vessel upon application of energy to the implant device. The system comprises one or more of such implant devices and also preferably comprises external energy-providing means, which are spatially separated from said implant devices and able to provide energy to said implant devices for increasing the temperature of the ablation regions of the implant devices up to an ablation temperature. In an embodiment, the implant device comprises a receiver coil for inducing a current in the ablation region of the implant, preferably to heat up the implant to an ablation temperature, under the influence of a varying magnetic field. In an embodiment, the external energy-providing means comprises a transmitter coil for generating a varying magnetic field.

The method of the present invention comprises inducing a current in the ablation region of the implant device by the external energy-providing means, said current heating up the ablation region, preferably through Joule heating, to an ablation temperature, thereby creating a circumferential lesion on the vessel wall. The lesion, or the scar tissue created by the lesion, can thereby form a signal-blocking circumferential path around the vessel wall.

The present invention improves on the prior art, in that the ablation region of the implant device comprises a circumferential diamond-like structure, and that the implant device comprises a support structure, which is attached to the diamond-like structure of the ablation region, the ablation region being on a proximal side of the implant device and the support region being on the distal side of the implant device. The circumferential diamond-like structure of the ablation region can substantially expand radially, thereby ensuring that a complete circumferential band along the vessel's inner wall is subtended. At the same time, the circumferential diamond-like structure can effectively form a lesion of two interconnected zig-zag loops around the vessel's wall, which increases the probability of creating a circumferential signal-blocking path. Furthermore, the circumferential diamond-like structure can act as a receiving coil in which a circumferential current can be induced by a time-varying magnetic field. Note that the circumferential diamond-like structure can be seen as forming a single winding with openings or as forming a double winding with interconnections.

Preferably the diamond-like structure is connected to the support region by means of a connecting segment. The connecting segment preferably comprises a set of essentially longitudinally arranged struts, which are preferably not interconnected in order to avoid forming a circumferential coil and thus to limit any induced current in the struts under the influence of a varying magnetic field along the longitudinal direction of the implant device. Such an arrangement allows positioning of the ablation region in the antrum of the PV, and holding it there under support of the supporting region which can be placed further down the PV. As a result, the ablation region can heat up to an ablation temperature necessary to ablate the tissue at the level of the antrum of the PV, while the support region does not result in an ablation of the tissue further down the PV because the support region does not heat up as much as the ablation region and/or the tissue of the PV at the position of the antrum is typically different from the tissue further down the PV, hence also the properties, including the temperature at which ablation can occur. Therefore, an implant device of the current invention allows to create a circumferential signal-blocking path at the correct location i.e. the antrum of the PV.

In a further aspect, the external energy-providing means are arranged to create a time-varying magnetic field comprising a frequency of lower than 20 MHz, preferably lower than 10 MHz, more preferably lower than 5 MHz, yet more preferably lower than 4, 3, 2 or 1 MHz. Most preferably, the frequency is at most 1 MHz, such as 1 kHz, 100 kHz, 200 kHz, 300 kHz, 400 kHz, 500 kHz, 600 kHz, 700 kHz, 800 kHz, 900 kHz, 1 MHz or any value therebetween. The inventors have found that the frequency at which the generated magnetic field varies in time has an optimal range for the present application, in particular for obtaining PVI. Contrary to expectation, the inventors have found that the optimal frequency does not necessarily coincide with the frequency at which energy losses or minimalized, but actually depends on the properties of human or animal tissue. Human and animal tissues of different types, in particular skin tissue, fat tissue such as subcutaneous or epicardial fat tissue, muscle tissue, etc. may respond differently to exposure to a time-varying magnetic field, and more importantly to a time-varying electromagnetic field, especially in terms of absorption or reflection characteristics. Furthermore, different people or animals will have different amounts of the different types of tissue. Hence, the inventors have found that the optimal frequency range for the present application of performing PVI corresponds to a frequency range wherein the response of the human or animal tissue is very small and/or stable (i.e. the response is essentially constant or varies only slightly for the different types of tissue), in particular with respect to absorption characteristics. The applicant has found that frequencies below 1 MHz are preferred. Without wishing to be bound by theory, the applicant believes that this is because below 1 MHz, all tissue has low and/or stable absorption characteristics, whereas above 20 MHz, most tissue seem to have high and/or highly variable absorption characteristics.

The frequency of the magnetic field should be such that the time-varying magnetic field created by the external energy-providing means can couple into the implant, more particularly into the receiver coil of the implant. This coupling should be high enough to allow the induced current to heat up the ablation region to the ablation temperature. Therefore, in an embodiment said frequency is at least 1 kHz.

In an embodiment, the self-expanding implant device comprises a resonance frequency at which an optimal transfer of power from external energy-providing means and implant can be achieved, i.e. coupling with minimal energy losses. This typically occurs if the frequency of the generated time-varying magnetic field coincides or is close to a resonance frequency of the implant or the receiver coil of the implant, which can depend on a large number of parameters. The resonance frequency of the implant may, however, depend on the degree and form of expansion of the implant device, and one needs to take into account a certain range of frequency range. Hence, in an embodiment, the frequency of the time-varying magnetic field is close to said resonance frequency of the implant device when the implant device is in an expanded position, preferably at least 5%, more preferably at least 25%, yet more preferably at least 50%, still more preferably at least 70%, yet more preferably at least 80%, even more preferably at least 90% of the resonance frequency of the implant device when the implant device is in an expanded position, and/or preferably at most 1000%, more preferably at most 500%, yet more preferably at most 250%, still more preferably at most 200%, yet more preferably at most 150%, even more preferably at most 110% of the resonance frequency of the implant device when the implant device is in an expanded position. Further, in view of the optimal frequency for performing PVI as discussed above, in a particularly preferred embodiment, the implant device comprises a resonance frequency which is between 1 KHz and 20 MHz, preferably lower than 10 MHz, more preferably lower than 5 MHz, yet more preferably lower than 4, 3, 2 or 1 MHz. Most preferably, the frequency is at most 1 MHz, such as 1 kHz, 100 kHz, 200 kHz, 300 kHz, 400 kHz, 500 kHz, 600 kHz, 700 kHz, 800 kHz, 900 kHz, 1 MHz or any value therebetween, when the implant device is in the expanded position.

Herein, the term "expanded position", in relation to the implant device, corresponds to the form and size of the self-expanding implant device when it is allowed to self-expand without being actively restricted in its expansion. This expanded position may be different than the shape and size of the implant when inserted and expanded within vessel. In fact, in order to ensure a good grip of the implant within the vessel, the implant in the expanded position generally is larger in size than and different in form to the implant when it is inserted and expanded inside the vessel.

In yet a further aspect, the present invention provides a method for calibrating a system comprising an implant and an external energy-providing means according to the present invention, said method comprising measuring the temperature in or near the vessel wall, preferably by means of an optical sensor close to or in contact with said vessel wall, before, during and/or after generating a pre-defined varying magnetic test field by said external energy-providing means. Preferably, the change in temperature in response of said test field is measured. Such a calibration method allows to better compute the magnitude and duration of the time-varying magnetic field which is necessary to heat up the ablation region to an ablation temperature. Hence, the present invention also concerns a method of computing the magnitude and duration of the time-varying magnetic field which is necessary to heat up the ablation region to an ablation temperature, taking into account the change in temperature as measured according to the method disclosed here above. The present invention also concerns a system comprising an implant, an external energy-providing means and a temperature sensor which is insertable into a vessel wall, said system preferably arranged to perform a method for calibrating or a method for computing the magnitude and duration of the time-varying magnetic field as disclosed herein.

The present invention thus also concerns a sensor catheter comprising near a distal end of said catheter a temperature sensor, preferably an optical sensor, for measuring the temperature of a vessel.

In an embodiment, the method of the present invention comprises measuring a varying magnetic field, preferably an alternating electromagnetic field, at the antrum of the PV and/or the position of the implant. Hence, the present invention also concerns a sensor for measuring a varying magnetic field, preferably an alternating electromagnetic field, at the antrum of the PV and/or the position of the implant, which is insertable into a PV via a catheter. Preferably the sensor comprises a pick-up coil positioned in the implant.

In a preferred embodiment, said sensor for measuring a varying magnetic field comprises a pick-up coil which is attached or attachable to or near a distal end of a sensor catheter. In a further embodiment, said sensor catheter also comprises an inflatable balloon at or near said pick-up coil for easy positioning and/or orienting of the pick-up coil and/or of the distal end of the sensor catheter.

In a preferred embodiment, said sensor catheter may be provided with both a sensor for measuring a varying magnetic field and a temperature sensor as described above and further below.

SHORT DESCRIPTION OF THE FIGURES

Figure 9:
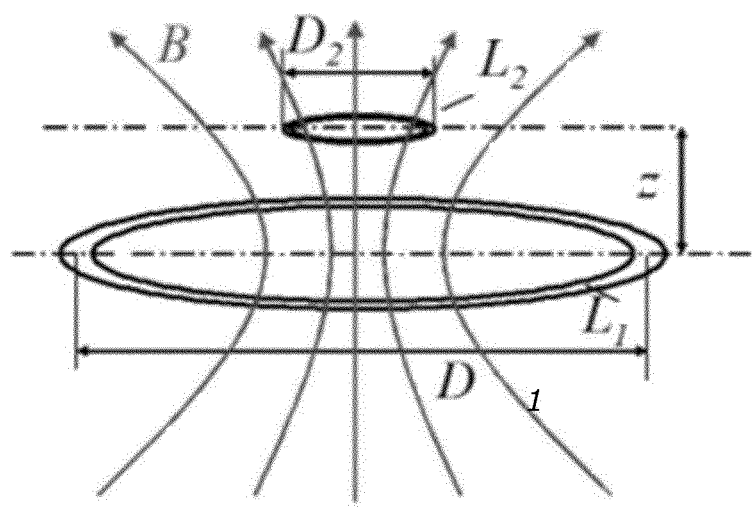

FIG. 9 shows a schematic drawing of an inductive coupled power transfer system. L1 is the primary coil with diameter D1, L2 is the secondary coil (in this case the implant in the pulmonary veins) with diameter D2. The efficiency of the power transfer depends on the coupling (k) between the inductors and their quality (Q). The coupling is determined by the distance between the inductors (z) and the ratio of D2/D1. The coupling is further determined by the shape of the coils, the angle between them and the used frequency.

Figure 10:
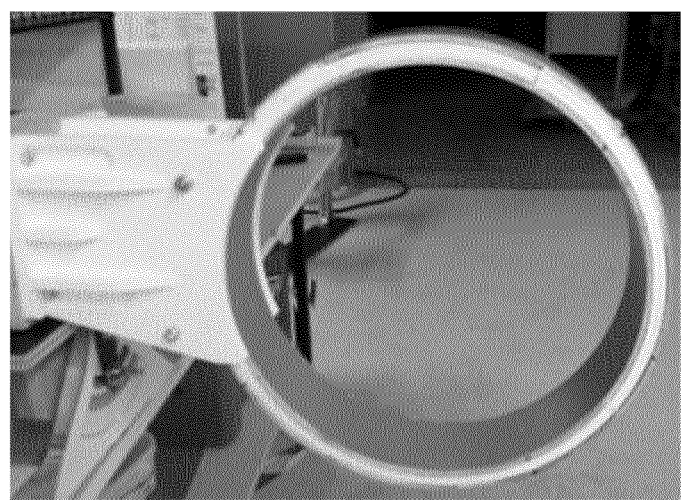

FIG. 10 shows a custom-made primary coil. The coil has 2 water-cooled copper windings, that are electrically insulated.

Figure 11:
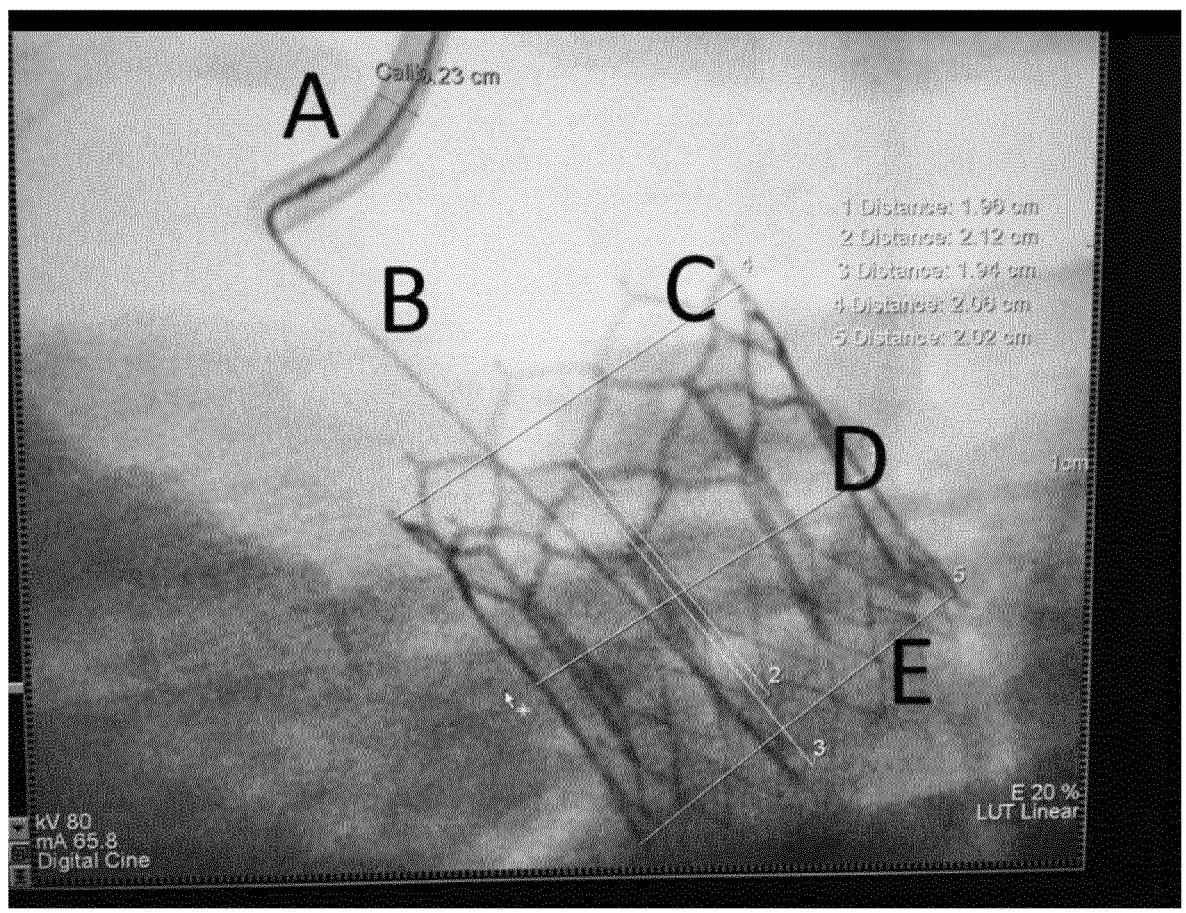

FIG. 11 shows an implant according to the present invention: (A) Delivery catheter (B) Guidewire (C) Heating segment with diamond-like struts that create resistance which allow current to be transformed into heat (D) Connecting segment (E) Support structure.

Figure 12:
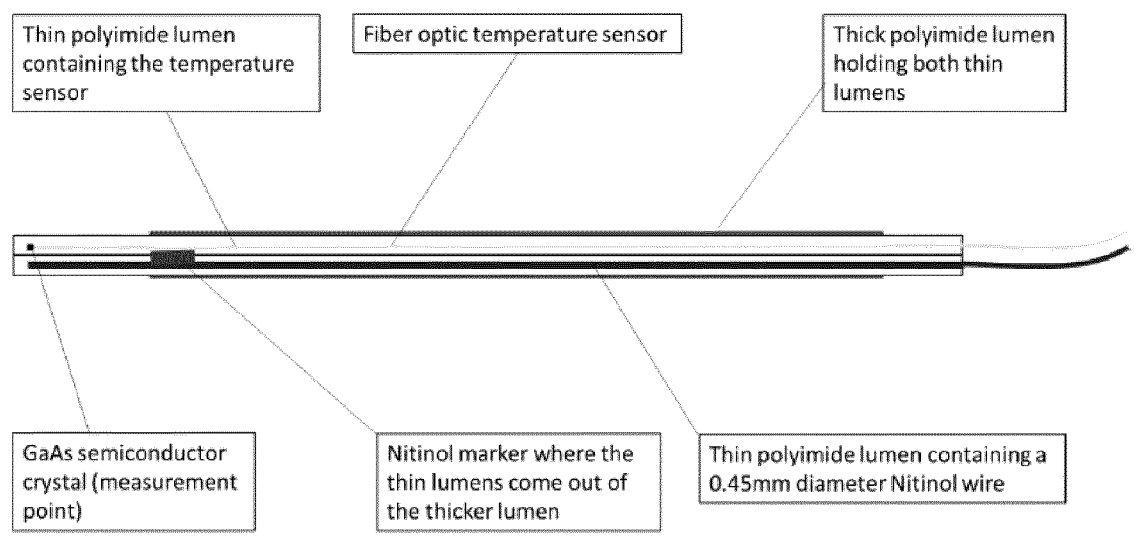

FIG. 12 shows a schematic structure of a temperature probe.

Figure 13:
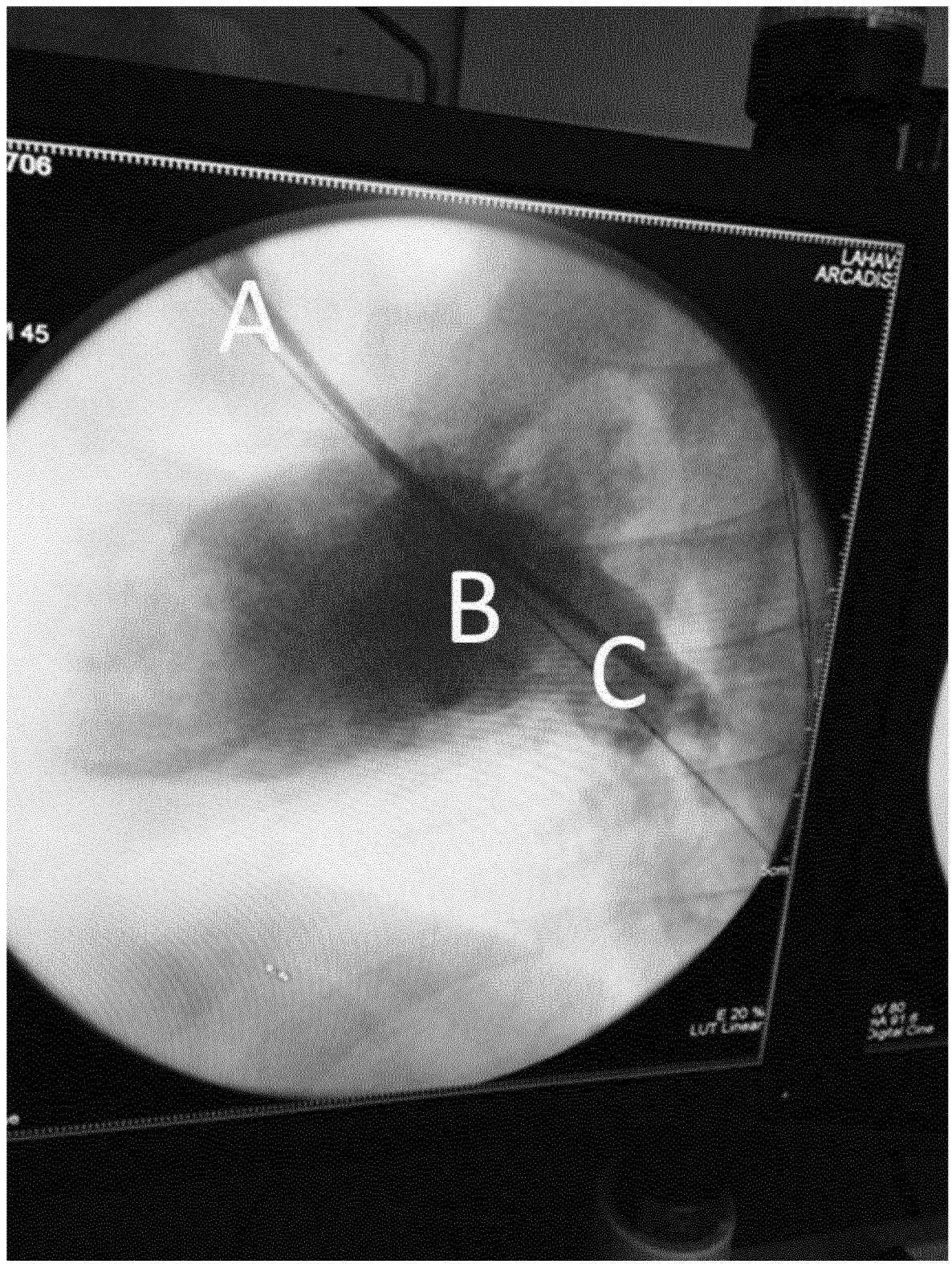

FIG. 13 shows a lateral view of left ventricle and atrium with (A) the transatrial sheath through which contrast dye is injected, (B) the left atrium and (C) the common ostium.

Figure 14:
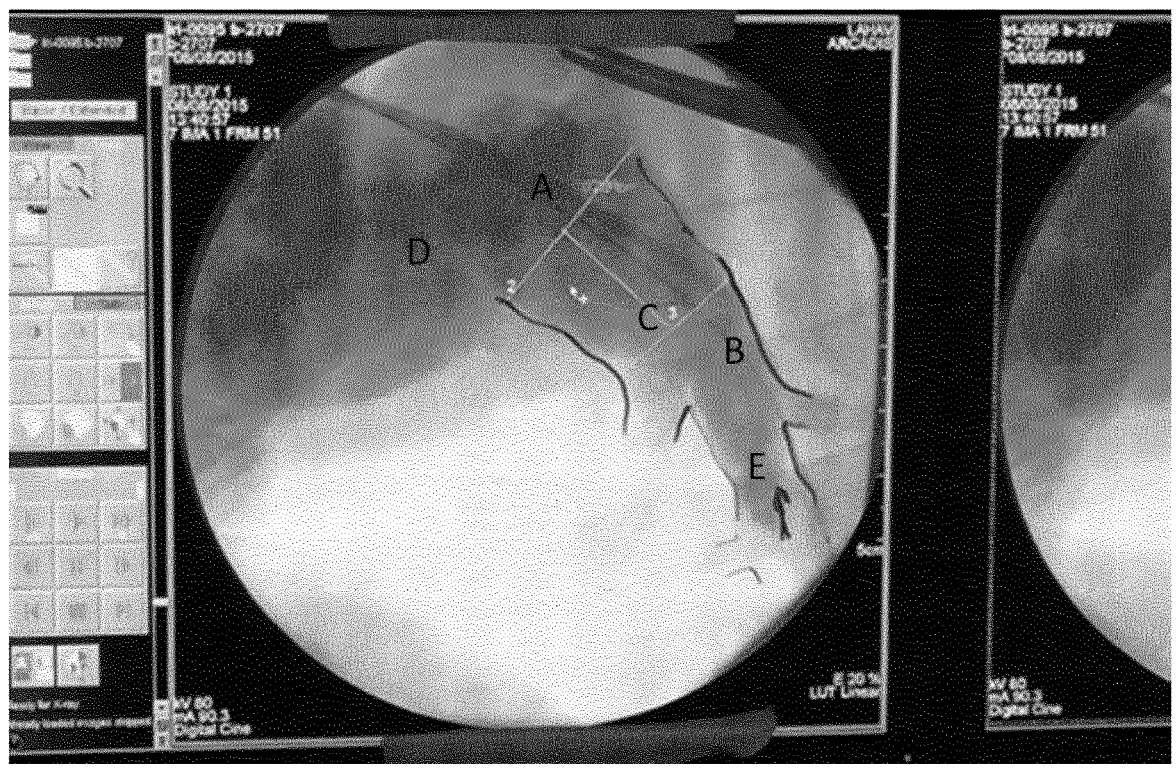

FIG. 14 shows an X-Ray image of the common inferior pulmonary vein of a 3 month old pig (mixture between landrace and large white) with (A) Guiding catheter to deliver the temperature probe to the PV wall, (B) Guidewire placed distally into the pulmonary vein, for delivery of the implant, (C) QCA measurements of the pulmonary veins, with size and length of the common inferior vein, (D) the left atrium, and (E) posterior branch of the pulmonary vein.

Figure 15:
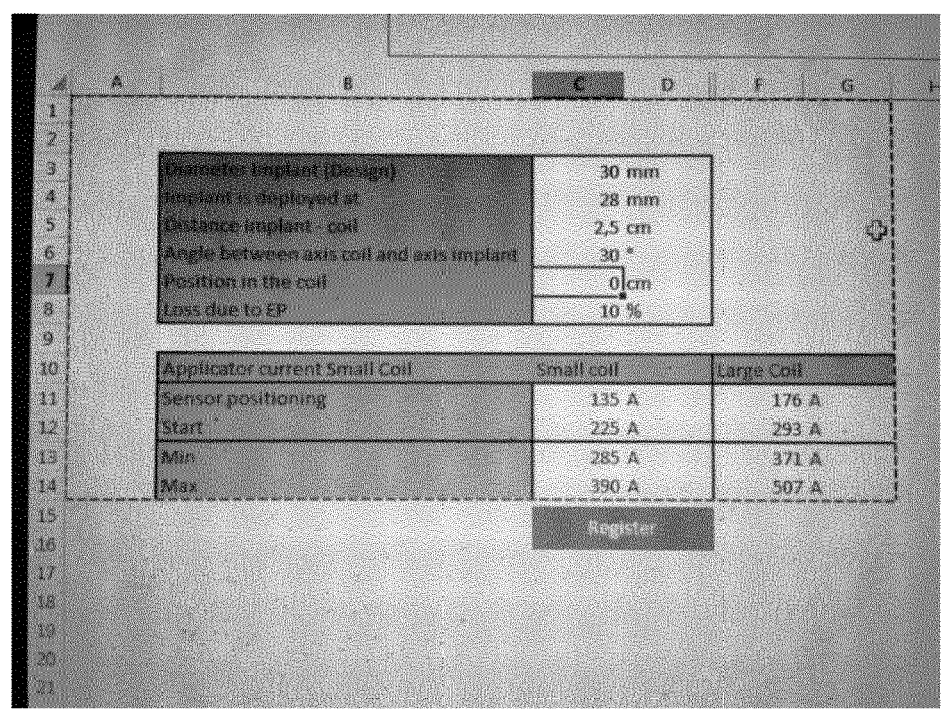

FIG. 15 shows an example of use of the proprietary algorithm, where different parameters are used as input, leading to the program providing a certain amperage that needs to be fed to the ablation coil.

Figure 16:
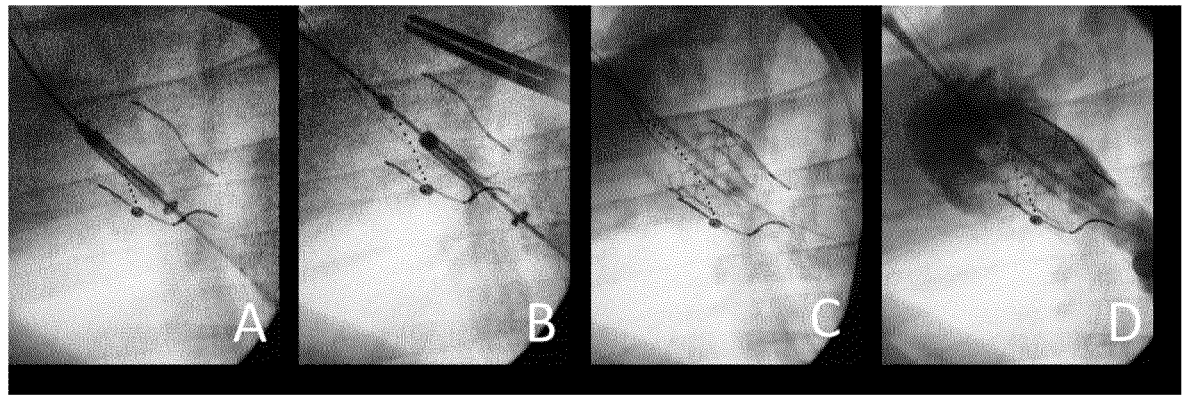

FIG. 16 shows the deployment of the implant into the common pulmonary vein. (A) Implant is positioned using the delineation of the pulmonary veins, the dotted line marks the position where the initial pacing was performed and served as a later reference. (B) Partial deployment with the distal fixation ring being deployed; (C) Fully deployed implant positioned in the pulmonary vein.

Figure 17:
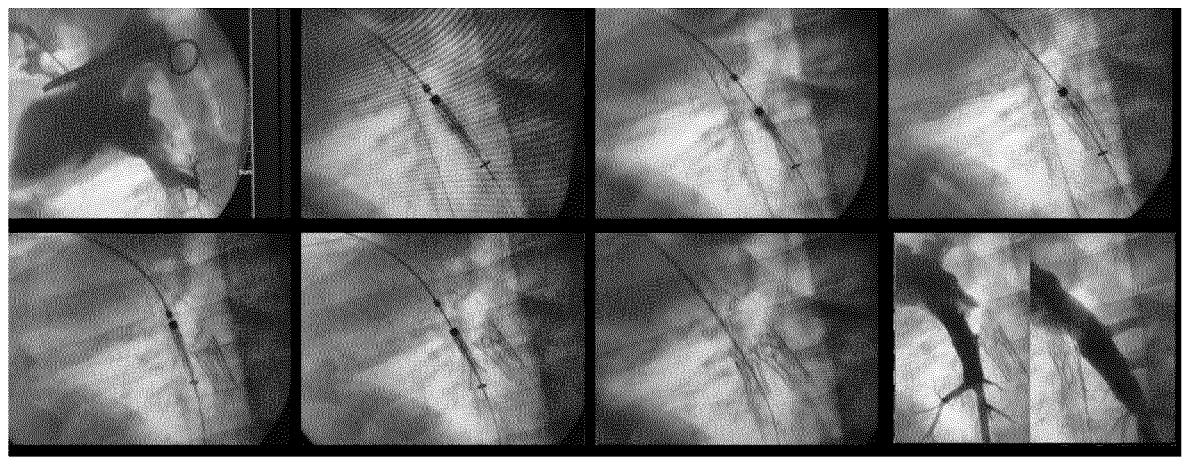

FIG. 17 shows the sequence with two consecutive implants being placed into the two inferior pulmonary veins (i.e. left and right) from upper left to lower right.

Figure 18:
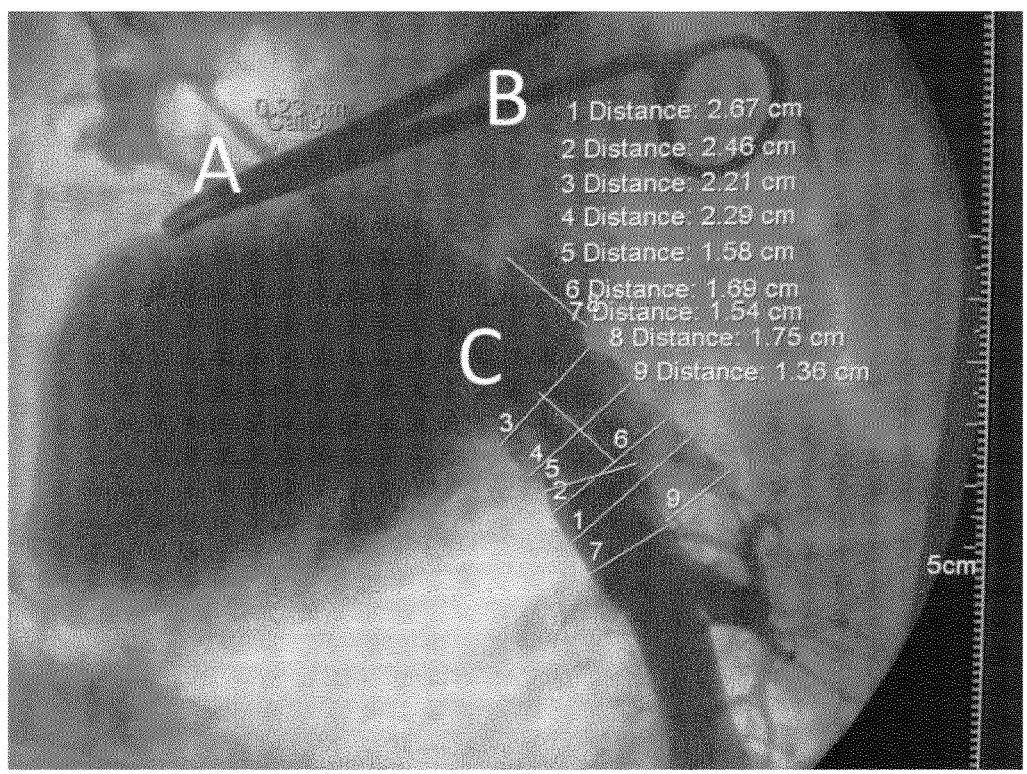

FIG. 18 shows a QCA of the inferior PV complex. (A) shows the reference measurement taken with the injection sheath (7 French) taken as actual reference, (B) shows the actual measurements and (C) the corresponding sites where the measurements were taken.

Figure 19:
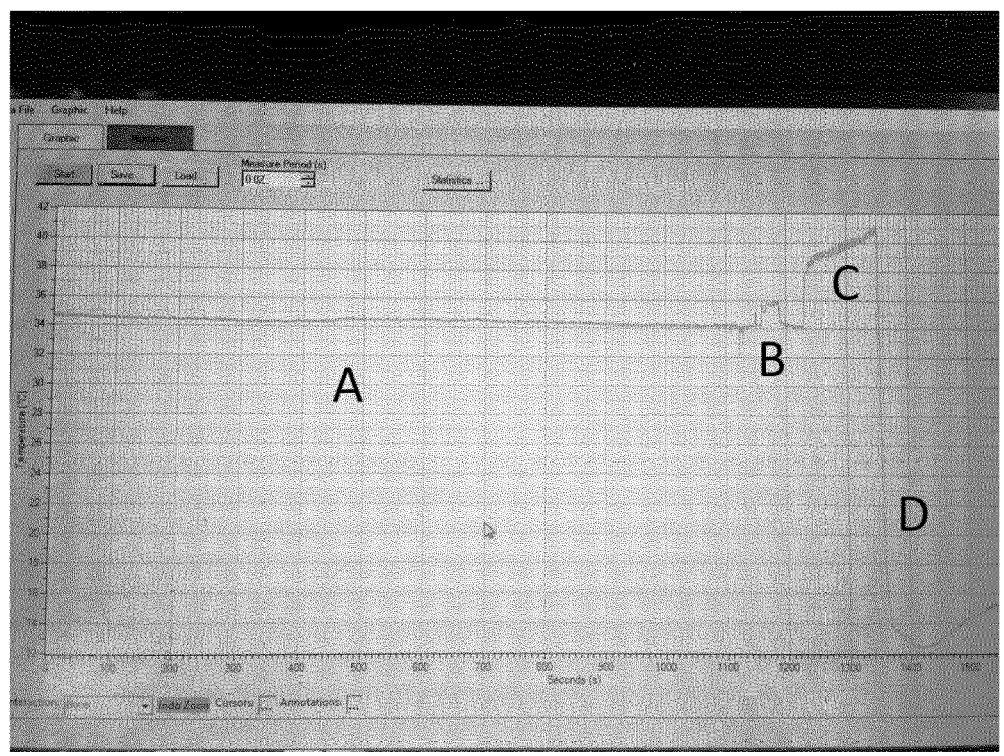

FIG. 19 shows a typical temperature-time curve during the ablation process. (A) Temperature monitoring during the preparation phase, the core temperature of the pig is about 35 degrees Celsius; (B) Test dose to find the optimum temperature registration point; temperature reaches 36 degrees Celsius; (C) Temperature registration during ablation. Temperature reaches 41 degrees Celsius; (D) Temperature upon removal of the temperature probe. The temperature probe is removed prematurely (after 120 seconds) to ensure also ablation of the small region where the temperature probe was fixed between the implant and the pulmonary vein wall.

Figure 20:
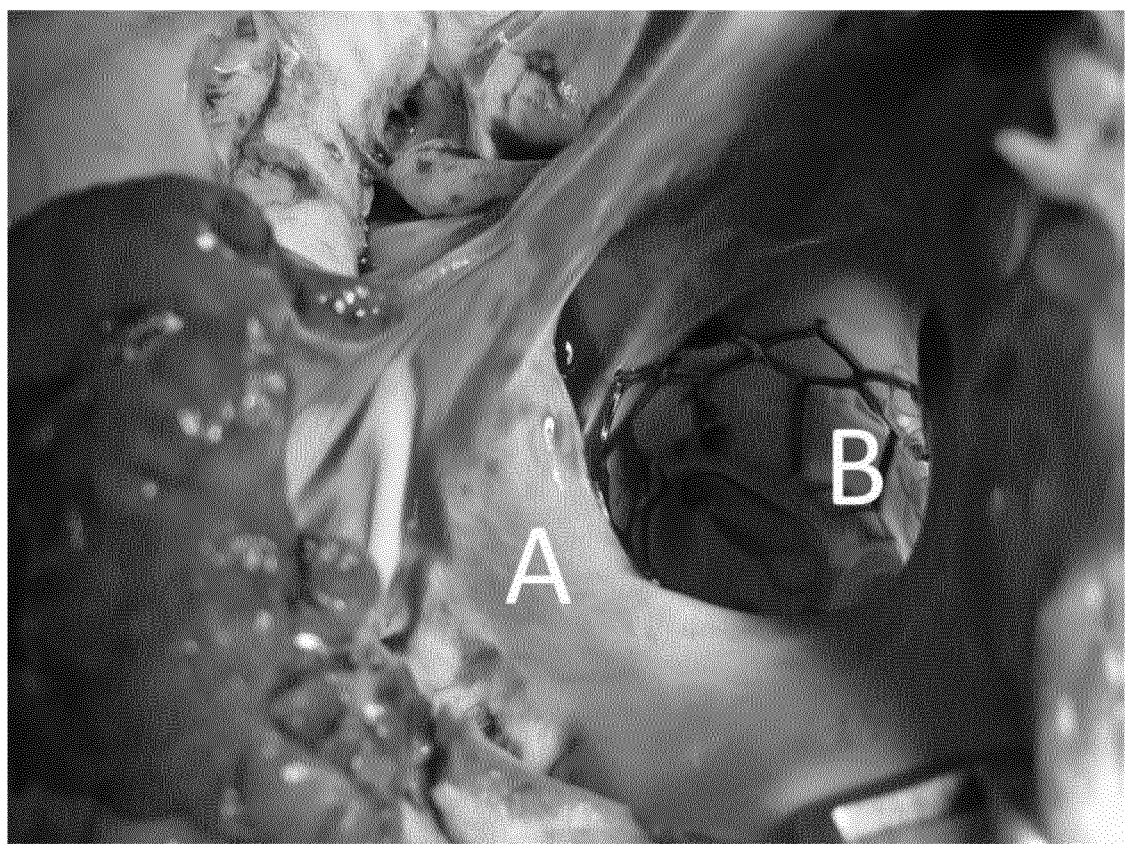
Figure 21:
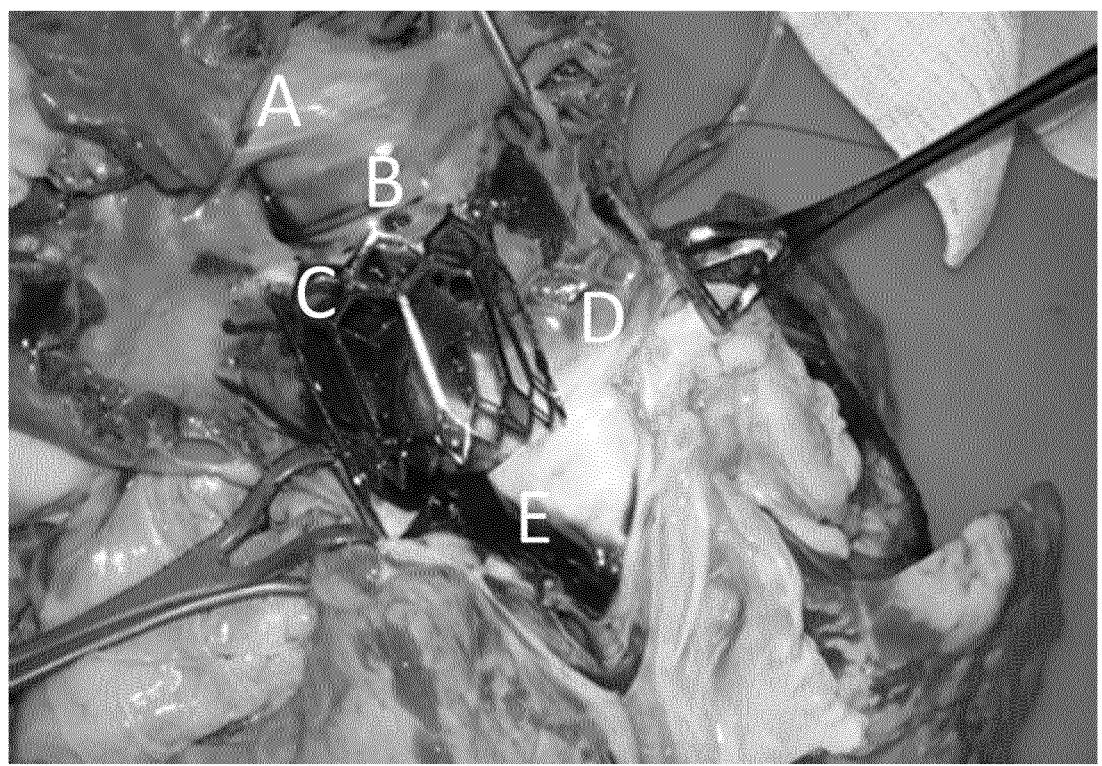

FIG. 20 shows a view into the left atrium after sacrifice of the animal. (A) shows the left atrium with the antrum and entrance to the pulmonary vein, (B) shows the pulmonary vein implant in situ FIG. 21 shows the left atrium opened from the anterior side. (A) Mitral valve (B) left atrium (C) original position of the implant with the diamond-shaped struts of the ablation ring (D) ablation zone in the pulmonary vein revealing the same diamond-like shape (E) distal pulmonary vein.

Figure 22:
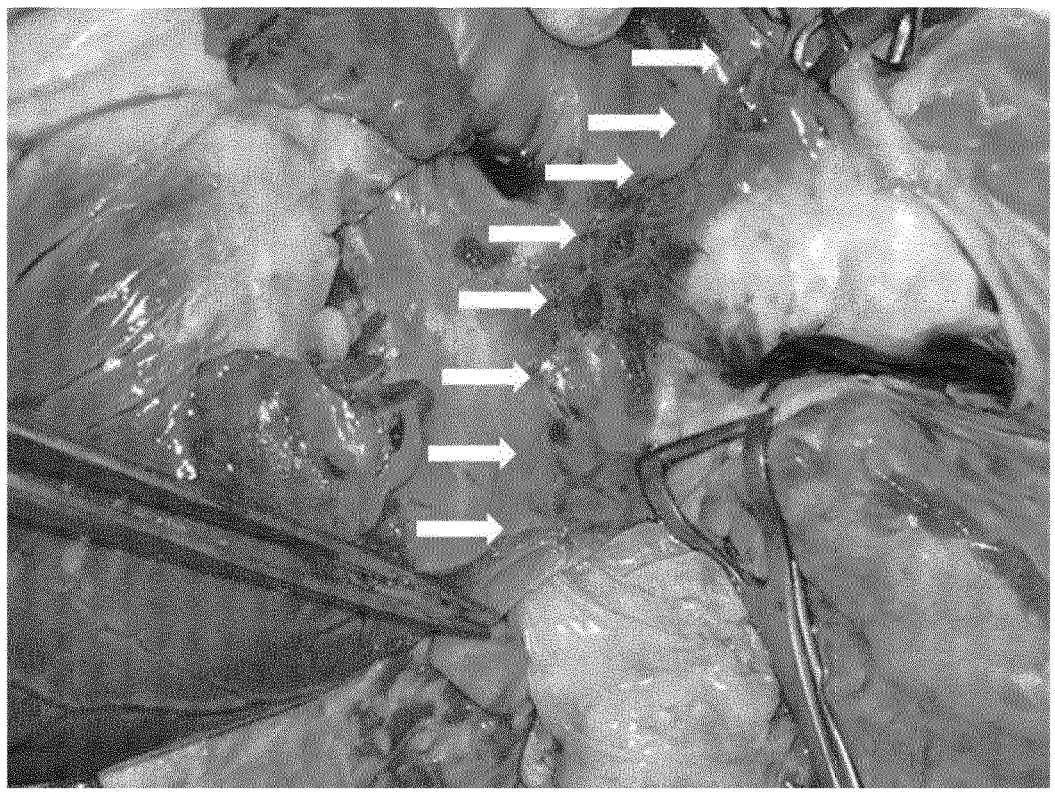

FIG. 22 shows an imprint of the implant after ablation and removal of the implant. This resulted in a continuous circumferential ablation zone in the transition zone between pulmonary vein and left atrium. The diamond-like shape of the ablation zone is clearly visible.

Figure 23:
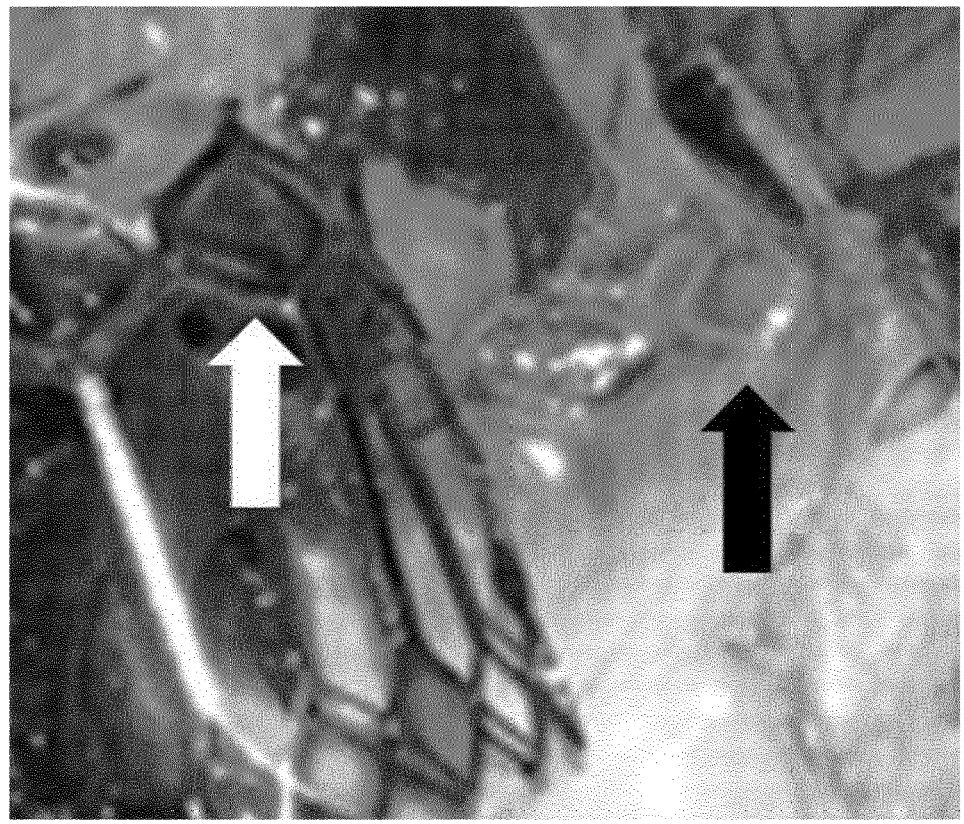

FIG. 23 shows a detail of the ablation zone. The white arrow shows the diamond-like shape of the struts of the ablation ring, the black arrow shows the matching ablation imprint. Mark that no ablation has occurred at the other sites of the pulmonary vein.

Figure 24:

FIG. 24 shows a detailed section of the ablated pulmonary vein of pig number 2. Clear demarcation of the ablation effect of a single strut of the implant (white arrows)

Figure 25:
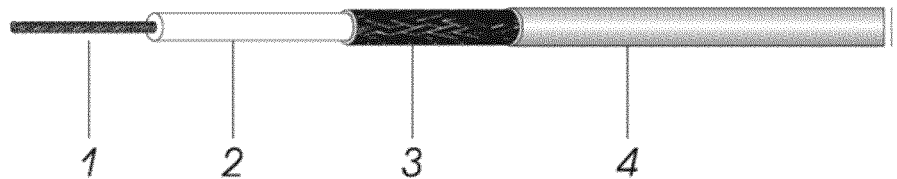

FIG. 25 shows a mini Coaxial cable 50Ω PRO POWER PP000843.

Figure 26:
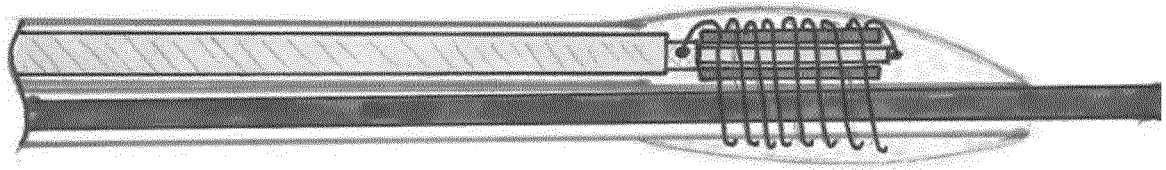

FIG. 26 shows a pick-Up Coil construction drawing.

Figure 27:
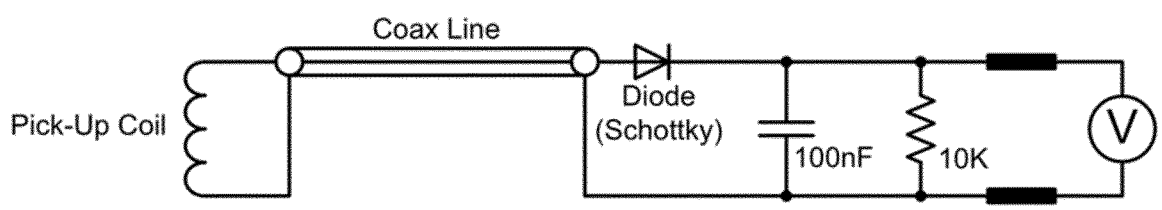
Figure 28:
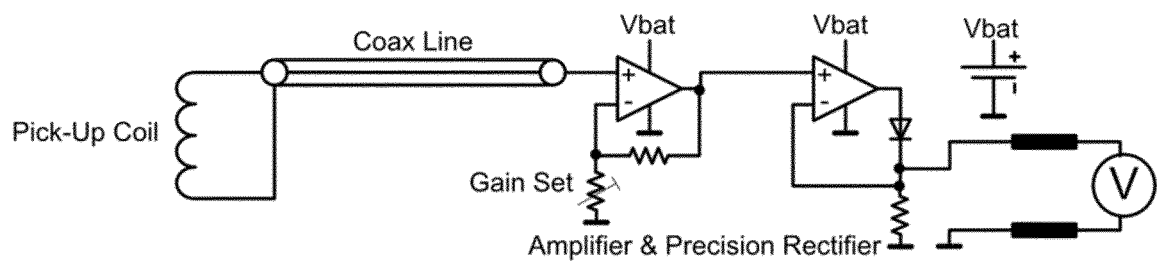

FIGS. 27 and 28 show circuits which can be used to process the measured field in the pick-up coil of a field sensor.

Figure 29:
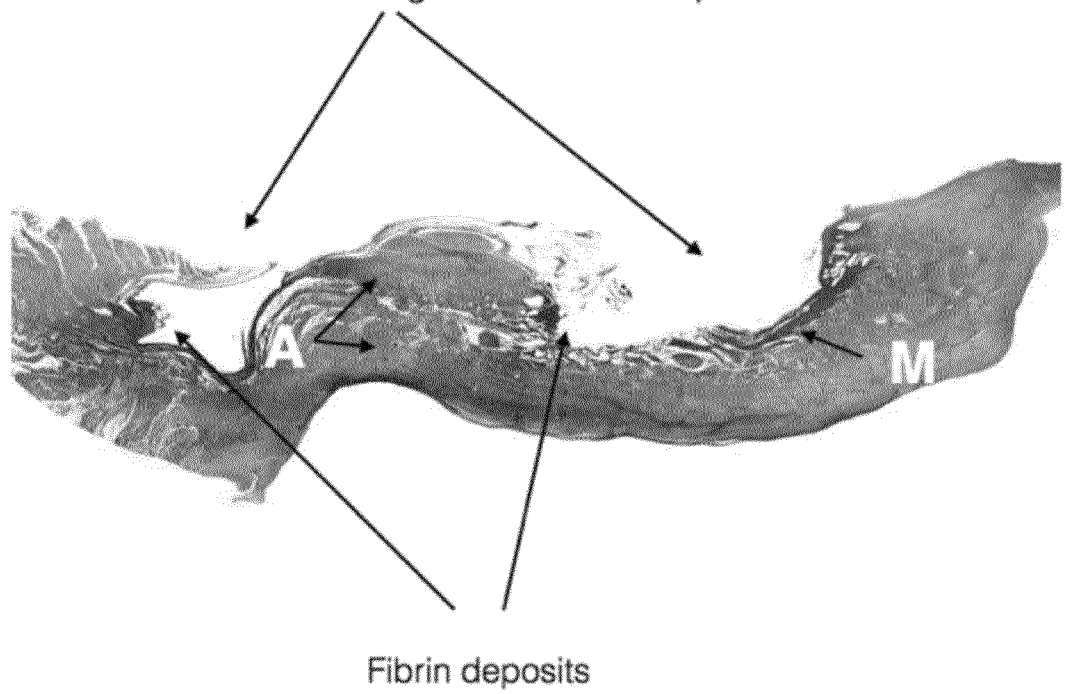

FIG. 29 shows transmural lesions following removal of the implant.

DETAILED DESCRIPTION OF THE INVENTION

Figure 1:
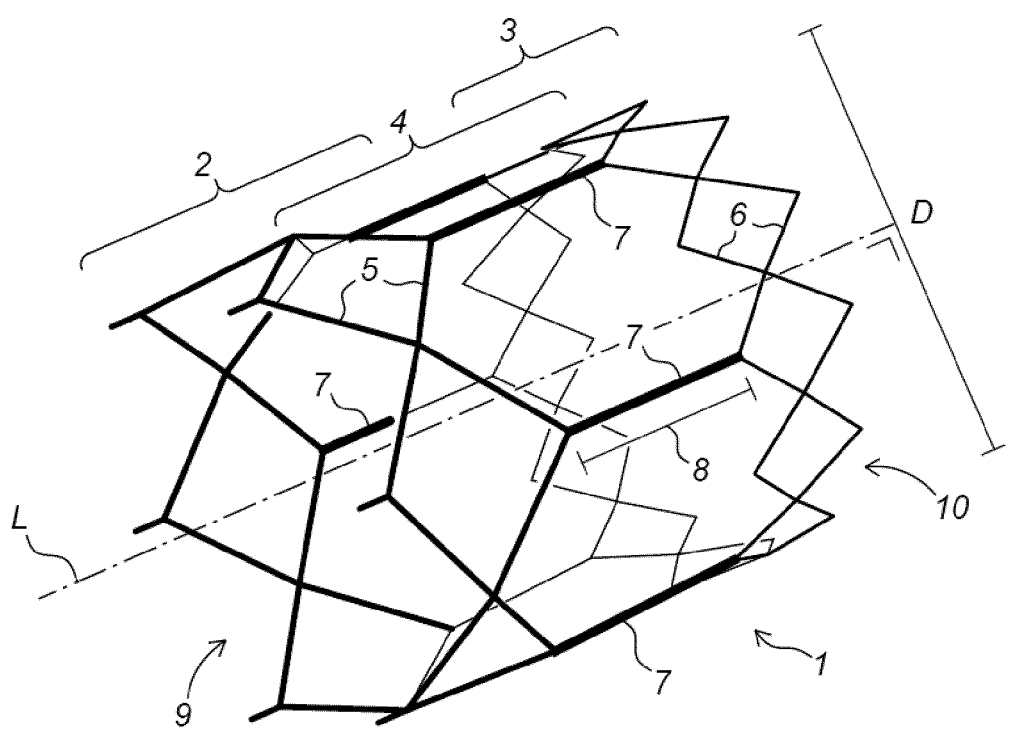
FIG. 1 shows a perspective view of an implant device according to the present invention, the implant device being in the expanded state.
Figure 2:
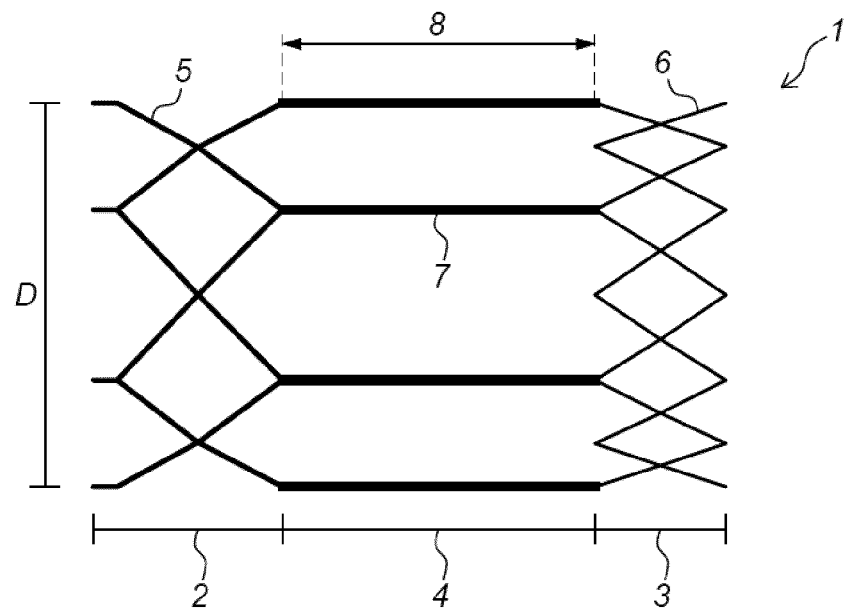
FIG. 2 shows a side view of an implant device according to the present invention, the implant device being in the expanded state.

FIGS. 1 and 2 show an embodiment of an implant device (1) according to the present invention in the expanded state. The implant device comprises proximal portion (2), a distal portion (3) and a connecting portion (4). The longitudinal direction (L) is also indicated. The proximal portion (2) and the distal portion (3) each comprise a radially self-expanding structure (5, 6). Preferably these self-expanding structures comprise a set of interconnected rhombus-like or diamond-like shaped elements made from a shape memory alloy (SMA) such as nitinol, the rhombus-like or diamond-like shaped elements being interconnected in such a way that they define a circumferential band-like region of the implant device. The connecting portion (4) comprises longitudinally oriented bendable struts (7), preferably at least 4, more preferably 6, which connect the self-expanding structure (5) of the proximal portion with the self-expanding structure (6) of the distal portion. In a fully expanded state, the implant device comprises a maximum implant diameter (D) along a direction perpendicular to the longitudinal direction (L). The struts (7) of the connecting portion comprise a strut length (8) along the longitudinal direction.

Preferably the strut length is between 5 mm and 30 mm, more preferably between 7 mm and 20 mm, such as 8, 9, 10, 11, 12, 13, 14, 15, 16, 17, 18, 19 mm or any value therebetween. Note that the strut length is measured when the implant device is in the fully expanded state. Although the strut length is substantially constant, small changes in the length of the struts can occur during deployment due to e.g. bending.

Preferably, the maximum implant diameter is between 5 mm and 50 mm, more preferably between 6 mm and 45 mm, yet more preferably between 7 mm and 40 mm, such as 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 mm or any value there between.

Preferably, the ratio between the strut length and the maximum implant diameter is at least 20%, more preferably at least 25%, still more preferably at least 30%, yet more preferably at least 35%, even more preferably at least 40%, even still more preferably at least 45%, yet still more preferably at least 50%.

The implant device comprises an implant length, as measured along the longitudinal direction.

In a preferred embodiment, said implant length is between 5 mm and 50 mm, more preferably between 6 mm and 45 mm, yet more preferably between 7 mm and 40 mm, such as 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 mm or any value there between.

In a preferred embodiment, the ratio between the strut length and the implant length is at least 20%, more preferably at least 25%, still more preferably at least 30%, yet more preferably at least 35%, even more preferably at least 40%, even still more preferably at least 45%, yet still more preferably at least 50%.

Figure 3:
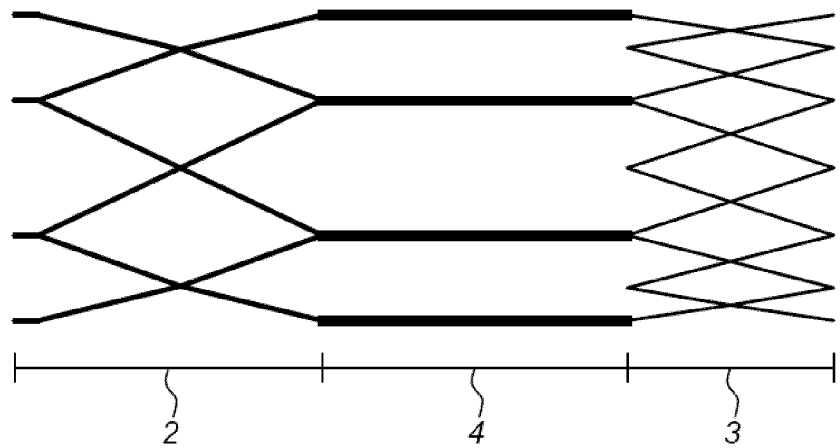
FIG. 3 shows a side view of an implant device according to the present invention, the implant device being in a semi-compressed state.
Figure 4:
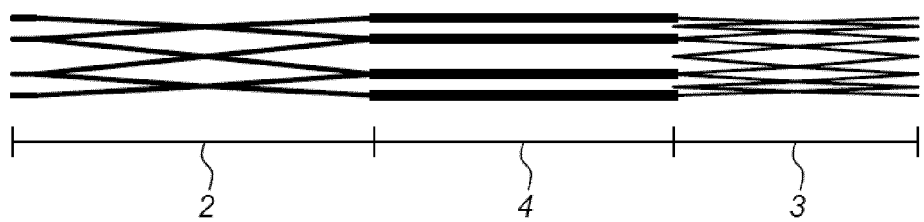
FIG. 4 shows a side view of an implant device according to the present invention, the implant device being in a fully compressed state.

FIG. 3 shows an embodiment of an implant device according to the present invention in a semi-expanded state, whereby the implant device has been partially compacted radially along its full length. One can note that the length of the proximal portion and the distal portion increases when being compacted, whereas the length of the struts essentially remains the same. This is also observed for the implant device in the fully compacted state as illustrated in FIG. 4. In this fully compacted state, the implant device can be placed in a delivery catheter system, preferably comprising a sheath to constrain the implant device to its compacted state.

Figure 5:
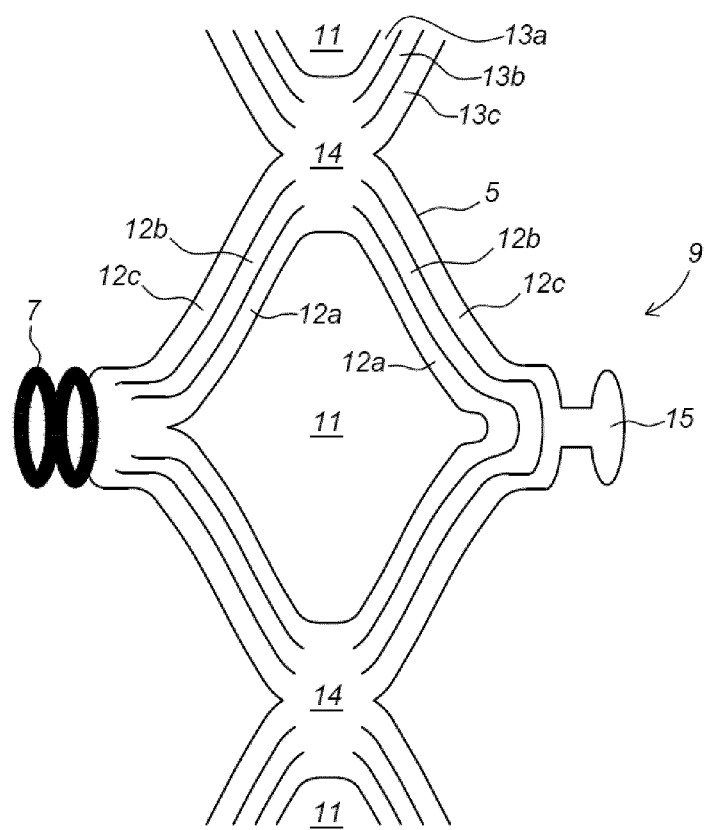
FIG. 5 shows an expanded view of a part of the proximal portion of an implant device according to the present invention.

An expanded view of the proximal portion is shown in FIG. 5. Note that the proximal end (9) is now to the right hand side of the figure. In a preferred embodiment, the self-expanding structure (5) of the proximal portion comprises a set of interconnected rhombus-like or diamond-like shaped elements, which allow the self-expansion of the proximal portion.

In a preferred embodiment, the diamond-like shaped element (11) is constructed from a set of wires or plaques (12a, 12b, 12c, 13a, 13b, 13c) defining the sides of the diamond-like shaped element (11). The wires or plaques are preferably made of SMA such as nitinol and contact each other, preferably they are pressed against each other due to the shape of the diamond-like element and the material properties of the SMA, thereby forming the sides of the diamond-like element (11). Different diamond-like elements (11) are preferably connected to each other in corresponding vertices (14).

The inventors have found that using a set of 2, 3 or more wires or plaques to form the sides of the elements (11) in the self-expanding structure allows to obtain a better ablation in a PVI procedure by e.g. heating of the proximal portion, said heating preferably done by external energy-providing means such as disclosed in WO 2012/131107 A1. Better ablation in this sense refers to a more complete circumferential ablation, thereby creating a circumferential signal-blocking path on the PV.

The self-expanding structure (5) of the proximal portion is attached on the struts (7) of the connecting portion. At the longitudinal end (9), the self-expanding structure preferably comprises a set of holding means, preferably comprising T-shaped teeth (15). These holding means (15) can be used to easily hold and transport the implant device in its compacted state with a delivery system through the lumen of a catheter to the target zone, the delivery system preferably comprising an implant holding head corresponding to the holding means such as the T-shaped teeth (15).

Figure 6:
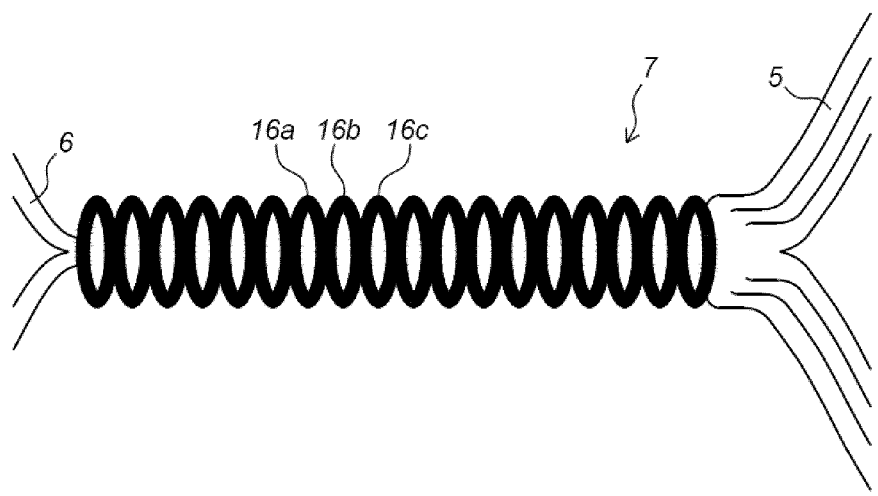
FIG. 6 shows an expanded view of a part of the connecting portion of an implant device according to the present invention.

An expanded view of a strut (7) is illustrated in FIG. 6. In a preferred embodiment, the struts (7) comprises a set of interconnected elements (16a, 16b, 16c) preferably comprising a ellipse-like shape or a diamond-like shape. These elements which are interconnected longitudinally allow an increased bendability of the strut such that it does not break when the implant device is in a semi-deployed state, i.e. the distal portion is expanded and the proximal portion is compacted. The struts are preferably made from SMA such as nitinol.

Figure 7:
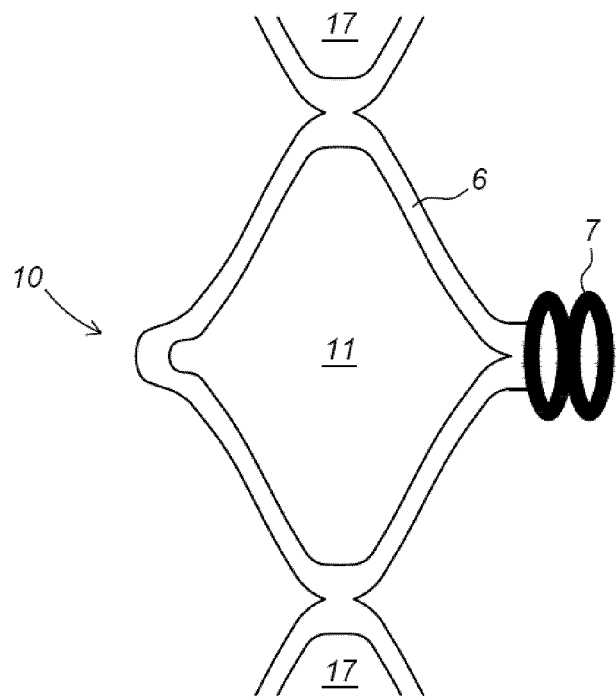
FIG. 7 shows an expanded view of a part of the distal portion of an implant device according to the present invention.

FIG. 7 shows an expanded view of the distal portion comprising the self-expanding structure (6). Also for this structure (6), a preferred embodiment comprises a set of interconnected rhombus-like shaped or diamond-like shaped elements (17). Preferably these elements (17) comprise sides comprising a wire or a plaque, preferably made of SMA such as nitinol, preferably at most 3 wires or plaques, more preferably at most 2 plaques, still more preferably only 1 wire or plaque. The inventors have found that, if the implant is used for PVI by ablation of a circumferential signal-blocking band on the PV, e.g. by heating the proximal portion, it is preferred that the distal portion does not get heated or at least not too much. The distal portion preferably provides anchoring of the implant device and its heating could thus create unwanted lesions.

Figure 8:
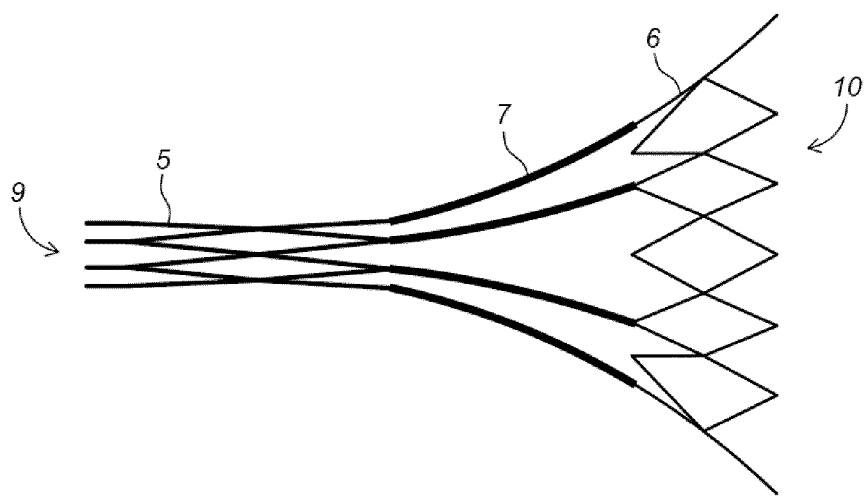
FIG. 8 shows a side view of an implant device according to the present invention when it is semi-deployed, i.e. whereby a distal portion is expanded and a proximal portion is still compressed.

FIG. 8 illustrates an implant device according to the present invention in a semi-deployed state, whereby the self-expanding structure (5) of the proximal portion is in a fully compacted state, and the self-expanding structure (6) of the distal portion is in an expanded or partially-expanded state. Hereby, one can note that, due to the bending of the struts and the large difference in diameter of the two self-expanding structures, the distal portion may comprise a diameter at the distal end which is larger than the maximum implant diameter, providing an even better anchoring of the implant during deployment than after deployment, thereby ensuring that the implant device does not move longitudinally during deployment.

In a preferred embodiment of the invention, the implant device comprises a receiver coil. Hereby, it is possible that the ablation region comprises or consists of a circumferential band-like region, e.g. the set of interconnected diamond-like shaped elements.

In a preferred embodiment of the invention, the power received by the implant comprising a receiving coil, is between 1 W and 55 W, preferably between 1 W and 50 W, more preferably between 2 W and 40 W, even more preferably between 3 W and 30 W, yet more preferably between 4 W and 25 W, still more preferably between 5 W and 20 W, such as 5 W, 6 W, 7 W, 8 W, 9 W, 10 W, 11 W, 12 W, 13 W, 14 W, 15 W, 16 W, 17 W, 18 W, 19 W, 20 W, or any value therebetween, most preferably between 10 W and 15 W. In a particularly preferred embodiment said power is received by the implant for a duration between 60 s and 300 s, preferably between 90 s and 270 s, more preferably between 120 s and 240 s, yet more preferably between 150 s and 210 s, most preferably around 180 s. The inventors have found that at such power value and for such durations, a circumferential lesion can be formed. The power which is received by the implant depends on a number of factors, including parameters such as (see also FIG. 18):
- diameters of the transmitting coil of the external energy-providing means and the receiving coil of the implant, in particular the diameter ratio,
- the relative position or orientation of the coils, in particular the angle between the axes of the coils,
- frequency of the transmitted magnetic field,
- amplitude of the transmitted magnetic field and/or power radiated by the transmitter coil.

In the present invention, the implant and the external energy-providing means can be adapted such that the power received by the implant is as described above.

Example 1: PVI in Pigs

In order to illustrate the system, devices and methods of the present invention, the techniques described herein were used on pigs, using a stent-based contactless energy transfer to isolate PVs in pigs.

Hereby, nitinol self-expanding implants were positioned in the pulmonary veins of pigs. Using electromagnetic wireless energy transfer principles, implants were heated in a controlled fashion. Using an electrophysiological sensing and pacing catheter, signals were checked before and after the ablation, and conduction block persistence acutely and after one month were checked. Eleven animals were successfully treated. Implantation and wireless energy transfer were safely performed in all animals. While pacing was successful in all animals prior to the ablation, conduction block was shown acutely in all eleven animals and chronically in seven animals. No periprocedural complications occurred, and the seven chronic animals remained in excellent shape until their sacrifice at one month. Histology confirmed the physical findings. Hence, the applicant has—for the first time—proven that complete isolation of pulmonary veins using a contactless externally applied energy source to correctly positioned implants is safe and feasible, and that long-term isolation of pulmonary veins can thus be accomplished. The procedure and results are disclosed in the following.

We investigated whether a self-expanding device can be delivered to the pulmonary veins (PV's), whether an approach of non-invasive ablation using electromagnetical energy transfer is safe and feasible, whether a long-term conduction block can be created and whether histology could confirm in-vivo findings.

1. METHODS a. Principals of Electromagnetical Energy Transfer (Inductive Power Transmission)

The heating of the implant (and consequent the ablation of tissue) in the pulmonary veins is performed through a contactless transfer of energy from a primary (or transmitter, L1 in FIG. 9) coil to a secondary (or receiver, L2 in FIG. 9, the implant in the PV) coil. Both coils form a system of magnetically coupled inductors. An alternating current in the transmitter coil generates a magnetic field which induces a voltage in the receiver coil. The efficiency of the power transfer depends on the coupling (k) between the inductors and their quality (Q). The coupling is determined by the distance between the inductors (z) and the ratio of the coil diameters $D_2/D_1$. The coupling is further determined by the shape of the coils, the angle between them and the used frequency.

The receiver coil should ideally be in the same plane as the transmitter coil for optimal power transfer. The diameter of the transmitter coil is defined by the diameter of the body. We constructed a coil of outer diameter 323 mm with an inner diameter of 305 mm which fits around a 65 kg pig, the size of our target animals. The diameter of the inner coil is defined by the diameter of the implant, between 15 and 35 mm. A large diameter transmitter coil and a small diameter receiver coil are not the ideal circumstances for optimal energy transfer, i.e. an energy transfer with minimal energy losses.

The energy delivered to the primary coil originates from a 400 V 3-phase mains supply. This supply is transformed by the converter (Easyheat 8310 LI, Ambrell, Scottsville, N.Y., USA) through the primary coil to generate the required electromagnetic field, which induces a current in the secondary coil. This current then—depending on the electrical properties of the coil material—creates heating of the secondary coil (the implant). Using the converter we can adjust the amount of electromagnetic energy created. The couple factor (the degree of energy transfer efficiency between coils) is approximately 2.1% at an operating frequency of 370 kHz. The couple factor decreases with the cosine (cos) of the angle when the receiver coil is tilted. See FIG. 10 which shows the custom-made primary coil.

Experimental data showed that a power of 10 W to 15 W is required in the implant during approximately 3 min to generate enough temperature to create a transmural lesion in ex-vivo experiments. The transmitter coil in the tests at hand consists of two windings. The receiver coil is a single winding and forms a short circuit ring. The couple factor between these two coils is approximately 2.1% at an operating frequency of 370 kHz, measured in the center of the transmitter coil. The required transmitter power is therefore between 476 W and 714 W in best circumstances. The couple factor will however decrease with the cosine (cos) of the tilt angle when the receiver coil is tilted. The required input power for successful ablation needs to increase accordingly. For example, a tilt of 45 degrees will lower the couple factor from 2.1% to 1.48% (Cos 45°=0.707). Transmit power subsequently needs to increase, up to 1014 W.

Resonance Principal for Power Generation

The required transmitter power can be generated in a resonant system. A coil with 2 windings and 323 mm diameter will have an inductance of L of approximately 2.68 µH. The ωL (2πfL) at 370 kHz of this coil is 6.23Ω. Currents of 250 to 300 Amp are required in the transmitter coil to generate the required heating currents in the Nitinol implant. A 560 kW generator would be required to feed this coil the conventional way.

The transmitter coil, together with two 150 nF capacitors, are connected in series to form a serial resonant circuit. The inductive and capacitive reactance (ωL and ωC) are equal in magnitude at the resonance frequency but cancel each other because they are 180° degrees apart in phase. Very high currents can run in this loop, virtually only limited by the Q factor, defined by the residual DC resistance of the construction and the damping. The required high current in the transmitter coil can now be generated with significantly reduced input power.

Resonance frequency f is defined by $$f = \frac{1}{2\pi\sqrt{LC}}.$$

The resonance frequency of this circuit is proximately 350 to 370 kHz. The resonance circuit is driven by an industrial radiofrequency (RF) heating generator (Ambrell, Scottsville, N.Y., USA). This generator is in principal capable of generating 10 kW of RF power in the frequency band 150 kHz to 400 kHz. The maximum generated power however depends on the limitations of the coil inductance and the matched resonance capacitors. The 2 winding coils required 75 nF to become resonant around 370 kHz. Two 150 nF capacitors were placed in series. The limitations of these capacitors are maximum 450 Amp and 1000 Vrms (2000V for the two capacitors in series).

The capabilities of the generator are further defined by the quality factor (Q) of the resonance circuit (especially the Q of the coil is important). The Q factor of the resonance circuit will be less than optimum when energy dissipative conductive material, e.g. a pig, is inserted in the coil. Tests showed that the maximum current in the transmitter coil was limited to approximately 270 A to 300 A with a 62 kg pig in the coil. The coil was custom-made and is shown in FIG. 10.

b. The Implant

As recurrence of atrial fibrillation due to reconnection following incomplete circumferential isolation of pulmonary veins seems to be the Achilles' heel of current catheter-based ablation techniques, we sought a solution that could provide us with a definite circumferential contact base.

We developed a self-expanding nitinol-based implant that ensures permanent fully circumferential contact with the PV wall; three different regions are distinguishable: the active heating part, the connection part and the stabilizing part (FIG. 11).

c. Temperature-Controlled Ablation

As the extent of thermal ablation is dependent upon duration of the ablation and the temperature reached locally, we decided to use temperature feedback to provide a measurement of the temperature between the ablation ring of the implant and the vein tissue. This measurement is considered to be close to the actual vein tissue surface temperature.

Since thermocouples and thermistors contain metals and are strongly influenced by the alternating electromagnetic fields, these devices are not suitable for this application. Optical sensors on the other hand do not contain metal, can be made very thin and light, and are not affected by magnetic fields in the radiofrequent or microwave band. We used the OpSens OTG-M170 fiberoptic sensor (OpSens, Quebec, Canada) for the temperature measurement. We used a two-lumen concept with the temperature sensor being able to move up and down, so that we were able to find the optimal position for temperature feedback (FIG. 12).

When activating the electromagnet using a test dose, small temperature increases were sought to determine the optimum position of the temperature sensor with respect to the implant.

d. The Animal Model

We chose the pig as model for catheterization of the pulmonary veins. The race chosen is a mixture between Land race and Large white. The animals were bred freely on a farm in Israel, where all the research was performed (Lahav Comprehensive Pre clinical Services, Lahav Kibbutz, Israel). Animals were scheduled to be between 3 and 4 months and to weigh between 60 and 65 kg. The age and size of the pigs was chosen so that they would fit inside the transmitter coil (that has an inner diameter of 30 cm).

All animals were preloaded with aspirin 300 mg and Plavix 300 mg from at least 24 h on beforehand, and were continued on aspirin 75 mg and Plavix 75 mg daily until termination of the trial.

e. The Procedure

Under full anesthesia, a left thoracic incision in lateral position was made, and a direct puncture of the left atrium was performed. A sheath was placed over a guidewire. A second guidewire was placed through the sheath. The sheath was taken out of the left atrium and put in place again, but now only over one of the two guidewires. This left us with a sheath with direct access to the left atrium (for placement of the temperature control system) and a guidewire for delivery of the implant.

A guiding catheter was brought into the left atrium, and contrast dye was injected to image the atrium and the pulmonary vein ostia (FIG. 13).

These images were fixed and used as a guide. Also, the outline of the pulmonary veins was drawn on the monitor, again as a guide. The pulmonary vein was then measured using a validated QCA system (Siemens, Munich, Germany) and the appropriate size of the implant was chosen. Implants were chosen so that they were at least 10% larger in diameter than the QCA measurement (FIG. 14).

Both guidewires were positioned distally into the common inferior vein, into the biggest of the two branches.

A diagnostic electrophysiology (EP) 10-pole steerable diagnostic EP catheter with a 10-pole connector (Viacath, Biotronik, Berlin, Germany) was placed into the pulmonary vein distally from the envisioned position of the ablation ring, and signals were recorded. Afterwards a pacing signal was sent through the same catheter, at a frequency of at least 120/min, or higher if necessary (depending on the heart rate of the animal), and the atrial/ventricular rates were recorded.

The temperature control catheter was then placed distally in the PV.

The implant was brought into the PV and positioned at the transition between muscular tissue of the very proximal PV and left atrium, and the non-muscular parts of the PV. The positioning of the implant was performed using angiography. The implant was then released. Correct positioning was again ensured using angiography.

After the implantation of the device, the angiography equipment was used so that the electromagnetic coil was positioned in exactly the same plane as the ablation ring of the implant.

Correct temperature probe positioning was then performed using an ablation test dose. When the correct position was confirmed, the temperature probe was fixed, and full ablation power was released during three minutes.

The power needed was calculated using a proprietary algorithm, which incorporates the size of the implant, the measured expansion, and the calculated deviation from the perfect alignment of device and ablation coil in the same plane (FIG. 15).

The temperature probe was removed after two minutes, to also ensure ablation of the small space where the temperature probe was positioned between the implant and the PV wall.

After the ablation, the position of the implant was again checked using angiography, to ensure the device had remained in the same position. The diagnostic 10-pole steerable diagnostic EP catheter with a 10-pole connector (Viacath, Biotronik, Berlin, Germany) was brought in exactly the same position as before device implantation. Signals were again measured and pacing was performed.

After removal of all catheters, 5 animals were sacrificed immediately, and 5 after one month. The animals that were kept alive one month were again catheterized, and conduction block patency checked. Heart and lungs were carefully inspected macroscopically, and specimens of the PV's were sent for histology.

Field Strength Measurement Inside the Ablation Ring Trough a Pick-Up Coil

In an embodiment, the method of the present invention comprises measuring a varying magnetic field, preferably an alternating electromagnetic field, at the antrum of the PV and/or the position of the implant. Hence, the present invention also concerns a sensor for measuring a varying magnetic field, preferably an alternating electromagnetic field, at the antrum of the PV and/or the position of the implant, which is insertable into a PV via a catheter. Preferably the sensor comprises a pick-up coiled positioned in the implant.

The quality of an ablation in progress can be monitored by measuring the temperature of the vain directly at the ablation point during the ablation cycle. The placement and adjustment of the (fibre-optic) temperature probe is a difficult task that requires high precision and skill.

An alternative method to generate feedback during the ablation is to use a miniature pick-up coil (probe) inserted in the vain and positioned in the implant.

The pick-up coil will sense the alternating electromagnetic field and send this signal to a measurement instrument trough a mini-coaxial cable.

The output signal of the coil depends on the applied field strength, the diameter of the pick-up coil, the number of windings, the core material and the location of the pick-up coil in the EM field.

An electronic circuit placed (external) at the end of the mini-Coax is used to transform the high frequent pick-up signal into a DC voltage. The circuit will calibrate the probe to compensate for possible production tolerances.

The miniature pick-up coil is visible by X-ray and can easily be brought into the correct position, guided over the available guide wire.

The guide wire is in the centre of the pick-up coil and will act as a core. The magnetic properties of the guide wire can influence the read-out voltage of the pick-up coil. The type of guide-wire should therefore be known. The electronic circuit can be set to compensate for different types of guide-wires if required.

The final output of the measurement circuit is a DC signal. This can be made visual by a simple voltmeter or a data logger. The output signal can be used to optimise the transmitter coil position at low field strength, prior to the actual ablation. The output signal can also be used as a feedback signal to adjust the generator power automatically.

The parameters of the optimum coil position and required ablation power can be logged, for every patient and every individual implant, at the time of implant placement. The ablation procedure can then be repeated later without feedback, based on the logged parameters at the time of the initial implant placement.

Materials Used for Prototype Build of Field Sensor 2 pcs MicroLumen Code 600-III, PTFE/PI length 1219 mm (48")
  Internal Diameter 1.524 mm (0.0600")/Polyimide Composite
  External Diameter 1.6789 mm (0.0661")/Polyimide
  Wall Thickness 0.0774 mm (0.00305")
  Manufacturer: MicroLumen, One Microlumen Way, Oldsmar, Fla. 34677 USA WWW.MICROLUMEN.COM
2 meter Mini Coaxial cable 50Ω PRO POWER PP000843
  See also FIG. 25.

The coil is wound over the inner conductor of the coax cable and the guide wire lumen (FIG. 10). A small PVC tube is used to increase the diameter of the coax inner conductor to approximately 1.5 mm.

Approximately 75 windings of close wound 0.15 mm CuI are applied. The coil ends are connected to the coax shield on one end and to the coax centre conductor on the other end. The coil length is approximately 17 mm.

The Lumen can be glued together and the tip is then to be covered with an insulating filler to protect the coil and to create a smooth tip.

Note: in the prototype a shrink sleeve was used instead to protect the pick-up coil and to create a smooth probe tip.

See also FIG. 26 for the construction of the pick-up coil.

Both Lumen having an internal diameter of 1.524 mm. A "supra Core 35" guide wire holds 0.89 mm diameter (Abbott REF 1002703-01). The lumen will pass this guide wire without any problem. A lumen with even a smaller diameter can be used for this. A smaller lumen for the coaxial cable can also be selected if a thinner Coax cable (Micro Coax) is used.

A simple rectifying circuit (FIG. 11) was used, during the first prototype tests, to convert the pick-up voltage into a DC signal. This enables a practical readout with a digital voltmeter. The measured voltage during coil alignment was approximately 1 Vdc with 100 Amp in the transmitter coil. The pick-up voltage increased to 3 and 4V during the actual ablation procedure (transmitter coil currents >300 Amp). See FIG. 27.

Smaller pick-up coils can also be used. Smaller coils however will pick-up less signal. An alternative circuit that amplifies the pick-up voltage, combines with a precision rectifier circuit or true RMS rectifier can be used as, e.g. shown in FIG. 28.

2. RESULTS

In total, 11 pigs were treated. In all animals the inferior common PV was chosen as ablation target. All procedures went fine and no major periprocedural complications occurred. In 10 animals we have placed a single implant, in one animal we placed two. A typical sequence of implantation of a device is shown in FIG. 16.

FIG. 17 shows the sequence with two consecutive implants being placed into the two inferior pulmonary veins (i.e. left and right) from upper left to lower right.

The sizes of the implants were chosen following QCA measurements of the inferior common PV, so that the implants were at least 10% larger than the PV. FIG. 18 shows an example of QCA measurements prior to the implantation.

Table 1 shows the procedural data. All implants were successfully positioned, in pig number 7 we placed 2 implants in two different pulmonary veins. In pig number 11 one implant dislocated from the PV due to undersizing of the implant. This did not lead to a major complication. Average duration of the procedure was 81±22 minutes.

TABLE 1

Procedural data

| Pig No | Age (mths) | Size (kg) | Common PV size (diameter, mm) | Implant size (mm) | Successful placement of implant (Yes/No) | Total procedural time (min) |
|---|---|---|---|---|---|---|
| 1 (2550) | 3 | 60 | 14 | 25 | Yes | 80 |
| 2 (2553) | 3 | 62 | 18 | 25 | Yes | 75 |
| 3 (2707) | 3 | 60 | 21 | 30 | Yes | 55 |
| 4 (2712) | 3 | 65 | 27 | 30 | Yes | 90 |
| 5 (2742) | 3 | 63 | 22 | 25 | Yes | 80 |
| 6 (2740) | 3 | 61 | 23 | 25 | Yes | 60 |
| 7 (2749) | 3 | 65 | 14 | 25 | Yes | 115 |
| (**) | | | 15 | 25 | Yes | |
| 8 (2545) | 3 | 62 | 21 | 25 | Yes | 85 |
| 9 (2546) | 3 | 63 | 13 | 25 | Yes | 125 |
| 10 (2548) | 3 | 63 | 22 | 25 | Yes | 70 |
| 11 (2708) | 3 | 61 | 23.5 (average of 20(distal) and 27 (proximal)) | 30 | Yes (*) | 60 |

(*) First implant in this animal dislocated from the PV into the left atrium.
(**) In pig number 7 two implants were positioned into two different pulmonary veins.

After implantation of the devices, the ablation coil was positioned over the animals, and positioning of the coil was done so, that the ablation coil and the implant were in the same plane. Deviations of the plane were fed into the algorithm described above, and power/current given was changed accordingly. Temperature measurements were performed following the above protocol. A typical temperature profile is shown in FIG. 19.

Table 2 shows the current provided to the ablation coil and the concurrent temperatures reached during the procedures. The average temperature increase generated in the vessel wall was 8.9±6.8° C. Duration of ablation was 200±201 seconds.

TABLE 2

Temperature and current data during testing and ablation, and total ablation time.

| Pig No | Core body temp. (° C.) | Positioning test dose temp. (° C.) | Positioning test dose current (A) | Optimal temp. reached (° C.) | Δ ° C. | Max Current (A) | Duration of ablation (sec) |
|---|---|---|---|---|---|---|---|
| 1 (2550) | 33.4 | 39.0 | 148.8 | 58 | 25.6 | 284 | 180 |
| 2 (2553) | 33.8 | None | 150.4 | 40 | 6.2 | 302.4 | 180 |
| 3 (2707) | 34.3 | 35.7 | 165.9 | 40 | 5.7 | 275.1 | 180 |

TABLE 2-continued

Temperature and current data during testing and ablation, and total ablation time.

| Pig No | Core body temp. (° C.) | Positioning test dose temp. (° C.) | Positioning test dose current (A) | Optimal temp. reached (° C.) | Δ ° C. | Max Current (A) | Duration of ablation (sec) |
|---|---|---|---|---|---|---|---|
| 4 (2712) | 33.5 | 35.2 | 243.6 | 38 | 4.5 | 390.0 | 180 |
| 5 (2742) | 35.9 | Dislocated temp sensor | NA | NA | | 396.0 | 180 |
| 6 (2740) | 35.1 | 36.0 | 207.9 | 39.0 | 3.9 | 401.1 | 180 |
| 7 (2749) | 35.1 | 36.5 | 310.8 | 40.0 | 4.9 | 399.0 | 180 |
|  | 35.1 | 36.0 | 310.8 | 37.0 | 1.9 | 399.0 | 180 |
| 8 (2545) | 35.5 | 35.8 | 140.8 | 49 | 13.5 | 300.8 | 300 |
| 9 (2546) | 36.0 | 42.0 | 201.6 | 49 | 13.0 | 270.4 | 300 |
| 10 (2548) | 35.4 | 39.0 | 150.4 | 52 | 13.0 | 284.0 | 180 |
| 11 (2708) | 33.7 | 35.0 | 133.3 | 40 | 6.3 | 354.1 | 180 |

Following the ablation, we used the 10-pole steerable diagnostic EP catheter with a 10-pole connector (Viacath, Biotronik, Berlin, Germany) to find signals distally into the PV, beyond the ablation zone. After recording these signals, pacing was performed at 120 beats/minute in the region distally from the ablation zone. Signals recorded and the effects of pacing distally from the ablation zone before and after the actual ablation process are shown in table 3.

TABLE 3

Results of sensing and pacing in the pulmonary veins before and after pacing.

| Pig No | Signals recorded pre-ablation | Conduction of paced signals pre-ablation | Signals recorded after ablation | Conduction of paced signals after ablation | Long term persistence of conduction block (1 month) |
|---|---|---|---|---|---|
| 1 (2550) | + | + | None (some echo after pacing) | − | + |
| 2 (2553) | + | + | None | − | + |
| 3 (2707) | + | + | Highly variable (200 ms-1200 ms) | − | + |
| 4 (2712) | + | + | Highly variable (250 ms-3000 ms) | − | + |
| 5 (2742) | + | + | None (some echo after pacing) | − | + |
| 6 (2740) | + | + | Highly variable (250 ms-3000 ms) | − | + |
| 7 (2749) | + | + | Highly variable (250 ms-3000 ms) | − | + |
|  | + | + | Highly variable (250 ms-3000 ms) | − | + |
| 8 (2545) | + | + | None | − | NA |
| 9 (2546) | + | + | None | − | NA |
| 10 (2548) | + | + | Highly variable (200 ms-2000 ms) | − | NA |
| 11 (2708) | + | + | Highly variable (250 ms-1000 ms) | − | NA | optimal temperature sensing zone, after which full ablation current could be applied. Also, in all animals, signals were detected distally from the envisaged ablation ring implantation, and pacing in that zone led to concurrent increase in heart frequency in all pigs, revealing perfect conduction. After ablation, the exact same location was again checked for signals, and pacing performed, and all 11 animals showed complete conduction block. The signals recorded in the isolated pulmonary veins showed a very variable cycle length between 250 ms and 3000 ms, which is entirely in line with the findings of Kabra et al. (7)

It is indeed the first time that energy delivery to perform ablation of pulmonary vein tissue was performed contactless. Of course, the whole procedure was not non-invasive, since implants still had to be delivered using invasive catheters.

The entire procedure took on average 81 minutes. This however included the positioning of the ablation coil around the animal, which, with all catheters being inside of the animal and sterility rules applying, proved cumbersome and often lasting 30-40 minutes. This means that significant reductions in time are possible. On the other hand, of course, for a complete isolation of all pulmonary veins, at least two Four animals were sacrificed immediately, seven were kept alive for one month. In the animals that were sacrificed immediately, we checked the ablation zone after removal of the implants for gross anatomical changes. A typical ablation zone is shown in FIGS. 20-24.

3. Conclusion

We have—for the first time—shown that complete isolation of pulmonary veins using a contactless externally applied energy source is safe and feasible. All eleven animals received nitinol self-expanding implants into the common ostium of the inferior pulmonary veins at the transition zone between left atrium and pulmonary vein without periprocedural complications. In all animals, sending a test current through the ablation coil, resulted in finding an implants would be needed in these animals, which would again increase the time expenditure.

We approached the pulmonary veins through the transatrial approach. This is for obvious reasons not the approach we want to have when applying this technology to humans. Transfemoral trials in animals are currently being performed.

There are of course issues to be resolved. We implanted one single device per animal, while in humans up to 4 implants may be needed to conclude a full pulmonary vein isolation. The implants are permanent, and some physicians may dislike the thought of placing four implants into the left atrium of a patient. Although the implants are light and do not contain an excess of nitinol, future developments may lead to partially resorbable implants. As PVI procedures today are still hampered with a high pulmonary vein stenosis rate (8), we believe this self-expanding implant that is positioned at the ostium will prevent recoil, spasm, retraction and stenosis formation as compared to current techniques. Long term follow-up on animals is underway to provide animal proof for that. Further, the temperature sensor was now placed adjacent to the implant, and was removed during the procedure. This may prove to be unpractical when more implants need to be placed into different pulmonary veins (as the temperature probe needs to be positioned through a separate guiding catheter). Other means for assessing the amount of energy delivered locally to the implant (and consecutively the temperature generated) are currently being developed.

Advantages of this technology over the existing ones however are numerous. Circumferential contact with the pulmonary vein after implanting a self-expanding nitinol device seems evident, thus creating a complete circumferential ablation lesion. However, the implant device, system and method according to the present invention have been illustrated to actually create such complete circumferential ablation lesions consistently. This is also illustrated in FIG. 29 showing transmural ablation lesions after removal of the implant. The inability to perform this appears to be the major set-back in current procedures, where the main reason for recurrence of AF seems to be reconnection of the pulmonary veins (9). Also, the actual ablation can be performed off-line, so that when the implants are positioned, the patient doesn't need to be in the cathlab to perform the ablation. This could significantly reduce cathlab time and thus allow for more patients being treated (many operators nowadays only perform two operations per cathlab per day). Further, complex mapping of signals does not appear to be needed anymore: the implants are positioned anatomically in all pulmonary veins, and ablation is performed without signal feedback being necessary. In addition, flexible electronics can be added to the implant, allowing for true temperature feedback during ablation, electrical signal recognition (for eventual reconnection diagnosis) and even detection and monitoring of true intracardiac electrocardiographic signals (to derive a true 12 lead—ECG) are a possibility.

In conclusion, we have demonstrated that in a relevant animal model, a self-expanding device can be delivered to the pulmonary veins (PV's) in a safe and feasible way, that energy can be delivered to the implant in a controlled fashion, and that a long-term conduction block can be created.

4. BIBLIOGRAPHY

In the example above, reference is made to the following documents:
1. Dang D, Arimie R, Haywood L J. A review of atrial fibrillation. Journal of the National Medical Association. 2002; 94(12):1036-48.
2. Cemin R, Manfrin M, Daves M, Rauhe W, Maggioni A P. Ten years differences in recently onset atrial fibrillation and flutter incidence and management. Monaldi Arch Chest Dis. 2014; 82(3):153-9.
3. Renoux C, Patenaude V, Suissa S. Incidence, mortality, and sex differences of non-valvular atrial fibrillation: a population-based study. J Am Heart Assoc. 2014; 3(6): e001402.
4. Camm A J, Lip G Y, De Caterina R, Savelieva I, Atar D, Hohnloser S H, et al. 2012 focused update of the ESC Guidelines for the management of atrial fibrillation: an update of the 2010 ESC Guidelines for the management of atrial fibrillation. Developed with the special contribution of the European Heart Rhythm Association. Eur Heart J. 2012; 33(21):2719-47.
5. Kirchhof P L G, Van Gelder I C, Bax J, Hylek E, Kaab S, Schotten U, Wegscheider K B G, Brandes A, Ezekowitz M, Diener H, Haegeli L, Heidbuchel H L D, Mont L, Willems S, Dorian P, Aunes-Jansson M, Blomstrom-Lundqvist C B M, Breitenstein S, Brueckmann M, Cater N C A, Dobrev D, Dubner S, Edvardsson N G, Friberg L, Goette A G M, Hatala R, Horwood J, Szumowski L, Kappenberger L, et al. Comprehensive risk reduction in patients with atrial fibrillation: emerging diagnostic and therapeutic options—a report from the 3rd Atrial Fibrillation Competence NETwork/European Heart Rhythm Association consensus conference. Europace. 2012; 14:8-27.
6. Camm A J. Atrial fibrillation and risk. Clin Cardiol. 2012; 35 Suppl 1:1-2.
7. Kabra R, Heist E K, Barrett C D, Donaldson D, Blendea D, Beinart R, et al. Incidence and electrophysiologic properties of dissociated pulmonary vein activity following pulmonary vein isolation during catheter ablation of atrial fibrillation. J Cardiovasc Electrophysiol. 2010; 21(12):1338-43.
8. Rostamian A, Narayan S M, Thomson L, Fishbein M, Siegel R J. The incidence, diagnosis, and management of pulmonary vein stenosis as a complication of atrial fibrillation ablation. J Intery Card Electrophysiol. 2014; 40(1): 63-74.
9. Anter E, Contreras-Valdes F M, Shvilkin A, Tschabrunn C M, Josephson M E. Acute pulmonary vein reconnection is a predictor of atrial fibrillation recurrence following pulmonary vein isolation. J Intery Card Electrophysiol. 2014; 39(3):225-32.

Example 2: PVI in Pigs, Further Trials

A further set of pig trials was conducted along similar lines as in the previous example for map the left atrium, implanting a dedicated nitinol-based self-expanding device, ablating the dedicated heating ring, remapping the left atrium after application of the ablation technology and evaluating acute histology.

In the procedure, the pigs are prepared and anesthetized. Catheterization is performed via a left intercostal incision.
During the procedure:
  one 6F sheath (to allow for the temperature optic sensors), one 8.5F Zurpaz (Boston Scientific) steerable guide or a 9F introducer, and one 6F sheath will be introduced into the left atrium;
  initial contrast fluid will be injected to image the left atrium and PV structure;

a 10-pole stimulation or pacing catheter shall be positioned into the PV distal from the target ablation zone;

signals in the PV will be measured;

pacing will be performed at a fixed rate above the pigs basic heart rate, typically above 100 beats/min. Atrial/ventricular response will be recorded to assess conduction intactness;

left atrium will be mapped using a Rythmia system (Boston Scientific). An Orian mapping catheter will be introduced via the 8.5F sheath to create a full map of the PVs;

guidewire will be introduced into left atrium through the 6F sheath with insertion into the inferior PV;

contrast fluid is introduced via a multipurpose catheter or directly via the 6F sheath;

Quantitative Coronary Angiography (QCA) measurements are performed to visualize PV structure;

appropriate implant device according to the present invention, with two self-expanding parts connected via longitudinal struts is selected (in particular with respect to its dimensions) based on QCA measurements, and is loaded into a delivery system;

fiberoptic temperature sensors on a sensor catheter are positioned near the target zone;

implant is positioned and released at the target zone;

signals in the PV are measured using a pacing catheter positioned distally in the PV from the target ablation zone;

sensor catheter with a field sensor for measuring the time-varying magnetic field is positioned within the implant, the pick-up coil of the magnetic field sensor is positioned beyond the distal end of the implant;

field strength is measured and temperature sensor is positioned more exact using a test dose from external coil positioned outside of the pig's body;

orientation of external coil is adapted in steps and field strength changes are measured by field sensor to optimize external coil orientation;

adequate power is generated by external coil to activate the ablation zone of the implant device;

temperature measurements are performed during ablation;

after about ½ of the ablation time, the temperature sensor is slowly withdrawn to ensure that the temperature sensor does not block ablation over a small region after the ablation procedure, signals in the PV are measured again using pacing catheter;

a new activation map with Orion catheter is obtained. If no clear signal blockage is shown by Rythmia, ablation procedure is repeated, optionally without temperature feedback or field feedback;

sacrifice of animal for performing histology.

Test Results

The trial was performed using 8 pigs. Two animals died during catheterization. 6 animals were successfully catheterized and an implant was placed. One of these six animals died suddenly after the implant was placed but before ablation was performed. Five animals underwent the ablation procedure, whereby between 5 to 55 W was delivered to the heating ring, i.e. the ablation zone of the implant, for between 90 s and 200 s. The Rythmia mapping system showed blocking of signals in PV after the ablation procedure. Histology performed after sacrifice of the animal showed none or only slight visual lesions, indicating that PVI can be achieved by the above ranges of power and time without drastic impact on the tissue.

The invention claimed is:

1. A self-expanding implant device (1) comprising a proximal portion (2) at a first longitudinal end, a distal portion (3) at a second longitudinal end opposite the first longitudinal end, and a connecting portion (4) between the proximal portion and the distal portion, wherein the proximal portion and the distal portion each comprise a radially self-expanding structure (5, 6), wherein the connecting portion comprises longitudinally oriented bendable struts (7), which directly connect the self-expanding structure of the proximal portion with the self-expanding structure of the distal portion, wherein in a fully expanded state, the self-expanding implant device comprises a maximum implant diameter (D) along a direction perpendicular to a longitudinal direction (L) and wherein the struts of the connecting portion comprise a strut length (8) along the longitudinal direction, and wherein the implant device has an implant length measured along the longitudinal direction;

wherein the strut length is such that when the self-expanding structure of the proximal portion is in a compacted state and the self-expanding structure of the distal portion is not constrained radially, the self-expanding structure of the distal portion reaches a semi-expanded state comprising a diameter which is at least 60% of the maximum implant diameter, wherein the struts are not interconnected, and wherein the strut length is between 5 mm and 20 mm, wherein the implant length is between 7 mm and 40 mm, and wherein the ratio of the strut length and the implant length is at least 50%;

wherein the self-expanding structure of the proximal portion comprises a set of interconnected diamond shaped elements;

wherein the self-expanding structure of the proximal portion at the longitudinal end comprises a set of holding means, comprising T shaped teeth (15).

2. The self-expanding implant device according to claim 1, wherein the diamond shaped element is constructed from a set of wires or plaques defining the sides of the diamond shaped element (11).

3. The self-expanding implant device according to claim 2, wherein the wires or plaques are made of a shape memory alloy (SMA) and contact each other.

4. The self-expanding implant device according to claim 1, wherein the self-expanding structure of the distal portion comprises a set of interconnected diamond shaped elements.

5. The self-expanding implant device according to claim 1, wherein the diamond shaped elements are interconnected in such a way that they define a circumferential region of the self-expanding implant device.

6. The self-expanding implant device according to claim 1, wherein the connecting portion comprises 4 struts.

7. The self-expanding implant device according to claim 1, wherein the maximum implant diameter is between 5 mm and 50 mm.

8. The self-expanding implant device according to claim 1, wherein at least one of the struts comprises a set of longitudinally interconnected elements comprising an ellipse shape or a diamond shape.

9. The self-expanding implant device according to claim 1, wherein the struts are made from SMA.

10. The self-expanding implant device according to claim 1, wherein the self-expanding implant device in the fully expanded state is tubular.

11. The self-expanding implant device according to claim 1, wherein the strut length is such that when the self-expanding structure of the proximal portion is in a compacted state and the self-expanding structure of the distal portion is not constrained radially, the self-expanding structure of the distal portion reaches a semi-expanded state comprising a diameter which is at least 90% of the maximum implant diameter.

12. The self-expanding implant device according to claim 1, wherein the strut length is such that when the self-expanding structure of the proximal portion is in a compacted state and the self-expanding structure of the distal portion is not constrained radially, the self-expanding structure of the distal portion reaches a semi-expanded state comprising a diameter which is more than 100% of the maximum implant diameter.

13. The self-expanding implant device according to claim 1, wherein the self-expanding implant device comprises an ablation region along at least a portion of its length.

14. The self-expanding implant device according to claim 13, wherein the self-expanding implant device is adapted to be implanted and deployed within a vessel, the ablation region being adapted for surface contact with the vessel and for subtending a circumferential band or a spiraling band and said ablation region effective to ablate a signal-blocking path within the vessel upon application of energy to the implant device.

15. The self-expanding implant device according to claim 13, wherein the ablation region comprises a circumferential diamond shaped structure on the proximal side of the self-expanding implant device, and wherein the self-expanding implant device further comprises a support structure on the distal side of the self-expanding implant device and attached to the diamond shaped structure of the ablation region.

16. The self-expanding implant device according to claim 13, wherein the self-expanding implant device comprises a receiver coil for inducing a current in the ablation region of the self-expanding implant device under the influence of a varying magnetic field.

17. An implant comprising a self-expanding implant device according to claim 1 and a delivery catheter system.

18. The implant according to claim 17, wherein the self-expanding structure of the proximal portion at the longitudinal end comprises a set of holding means comprising T shaped teeth (15), and wherein the delivery catheter system comprises an implant holding head corresponding to the holding means of the self-expanding implant device.

19. The self-expanding implant device according to claim 1, wherein the self-expanding structure of the proximal portion is made of SMA.

20. The self-expanding implant device according to claim 19, wherein the SMA is nitinol.

21. The self-expanding implant device according to claim 2, wherein the set of wires or plaques defining the sides of the diamond shaped element (11) comprises 2 wires or plaques.

22. The self-expanding implant device according to claim 21, wherein the set of wires or plaques defining the sides of the diamond shaped element (11) comprises 3 wires or plaques.

23. The self-expanding implant device according to claim 3, wherein the SMA is nitinol.

24. The self-expanding implant device of claim 9, wherein the SMA is nitinol.

25. The self-expanding implant device according to claim 4, wherein the self-expanding structure of the distal portion is made of SMA.

26. The self-expanding implant device according to claim 25, wherein the SMA is nitinol.

27. The implant of claim 17, wherein said delivery catheter system further comprises a sheath.

* * * * *